US011045289B2

(12) United States Patent
Karmon

(10) Patent No.: US 11,045,289 B2
(45) Date of Patent: Jun. 29, 2021

(54) DEVICES AND METHODS FOR ELEVATING THE SCHNEIDERIAN MEMBRANE

(71) Applicant: Ben Zion Karmon, Petach-Tikva (IL)

(72) Inventor: Ben Zion Karmon, Petach-Tikva (IL)

( * ) Notice: Subject to any disclaimer, the term of this patent is extended or adjusted under 35 U.S.C. 154(b) by 272 days.

(21) Appl. No.: 16/066,008

(22) PCT Filed: Jun. 15, 2016

(86) PCT No.: PCT/IL2016/051339
§ 371 (c)(1),
(2) Date: Jun. 25, 2018

(87) PCT Pub. No.: WO2017/115350
PCT Pub. Date: Jul. 6, 2017

(65) Prior Publication Data
US 2019/0008615 A1    Jan. 10, 2019

(30) Foreign Application Priority Data
Dec. 29, 2015 (IL) .......................................... 243401

(51) Int. Cl.
*A61C 8/00* (2006.01)
*A61M 25/10* (2013.01)
*A61M 25/00* (2006.01)

(52) U.S. Cl.
CPC .......... *A61C 8/0092* (2013.01); *A61C 8/0089* (2013.01); *A61M 25/10* (2013.01); *A61M 2025/0092* (2013.01)

(58) Field of Classification Search
CPC ............... A61C 8/0092; A61C 8/0089; A61M 2025/0092
See application file for complete search history.

(56) References Cited

U.S. PATENT DOCUMENTS

| 3,640,278 A | 2/1972 | Freidman |
| 3,800,788 A | 4/1974 | White |
| 3,875,595 A | 4/1975 | Froning |

(Continued)

FOREIGN PATENT DOCUMENTS

| CN | 1125559 A | 7/1996 |
| DE | 4321785 C1 | 3/1995 |

(Continued)

OTHER PUBLICATIONS

Notice of deficiencies in Israeli patent application No. 243401 from Israeli Patent Office filed on Jul. 18, 2016.

(Continued)

*Primary Examiner* — Ralph A Lewis

(57) ABSTRACT

Devices and methods to perform elevation of the Schneiderian membrane in a safe, easy and minimally invasive manner are described. The devices include a cannula and a balloon. A liquid can be introduced through the cannula inside the maxillary sinus below the Schneiderian membrane to elevate the Schneiderian membrane. The balloon can be inflated through the cannula so the balloon will be expanded inside the maxillary sinus below the Schneiderian membrane while being surrounded by the liquid which was previously introduce inside the maxillary sinus. The expansion of the balloon is safely further elevating the Schneiderian membrane in a controlled amount and location.

20 Claims, 13 Drawing Sheets

(56) References Cited

U.S. PATENT DOCUMENTS

| | | |
|---|---|---|
| 3,924,274 A | 12/1975 | Heimke et al. |
| 4,313,434 A | 2/1982 | Segal |
| 4,430,760 A | 2/1984 | Smestad |
| 4,431,416 A | 2/1984 | Niznick |
| 4,501,266 A | 2/1985 | McDaniel |
| 4,521,192 A | 6/1985 | Linkow |
| 4,627,434 A | 12/1986 | Murray |
| 4,653,489 A | 3/1987 | Tronzo |
| 4,665,918 A | 5/1987 | Garza et al. |
| 4,682,951 A | 7/1987 | Linkow |
| 4,686,985 A | 8/1987 | Lottick |
| 4,690,684 A | 9/1987 | McGreevy et al. |
| 4,740,207 A | 4/1988 | Kreamer |
| 4,744,754 A | 5/1988 | Ross |
| 4,755,184 A | 7/1988 | Silverberg |
| 4,768,507 A | 9/1988 | Fischell et al. |
| 4,787,906 A | 11/1988 | Haris |
| 4,798,205 A | 1/1989 | Bonomo et al. |
| 4,824,436 A | 4/1989 | Wolinsky |
| 4,832,688 A | 5/1989 | Sagae et al. |
| 4,843,112 A | 6/1989 | Gerhart et al. |
| 4,863,472 A | 9/1989 | Tormala et al. |
| 4,878,906 A | 11/1989 | Lindemann et al. |
| 4,922,905 A | 5/1990 | Strecker |
| 4,929,247 A | 5/1990 | Rayhack |
| 4,950,227 A | 8/1990 | Savin et al. |
| 4,969,888 A | 11/1990 | Scholten et al. |
| 4,994,298 A | 2/1991 | Yasuda |
| 5,005,591 A | 4/1991 | Austad |
| 5,020,525 A | 6/1991 | Ewing et al. |
| 5,059,194 A | 10/1991 | Michelson |
| 5,077,076 A | 12/1991 | Gonsalves et al. |
| 5,102,413 A | 4/1992 | Poddar |
| 5,108,404 A | 4/1992 | Scholten et al. |
| 5,108,416 A | 4/1992 | Ryan et al. |
| 5,146,933 A | 9/1992 | Boyd |
| 5,152,747 A | 10/1992 | Olivier |
| 5,156,605 A | 10/1992 | Pursley et al. |
| 5,158,548 A | 10/1992 | Lau et al. |
| 5,180,380 A | 1/1993 | Pursley et al. |
| 5,192,307 A | 3/1993 | Wall |
| 5,234,457 A | 8/1993 | Andersen |
| 5,242,399 A | 9/1993 | Lau et al. |
| 5,254,089 A | 10/1993 | Wang |
| 5,286,261 A | 2/1994 | Roizenblatt |
| 5,304,117 A | 4/1994 | Wilk |
| 5,306,286 A | 4/1994 | Stack et al. |
| 5,308,350 A | 5/1994 | Mikhail |
| 5,350,580 A | 9/1994 | Muchow et al. |
| 5,372,583 A | 12/1994 | Roberts et al. |
| 5,376,123 A | 12/1994 | Klaue et al. |
| 5,380,329 A | 1/1995 | Elia et al. |
| 5,397,235 A | 3/1995 | Elia |
| 5,405,322 A | 4/1995 | Lennox et al. |
| 5,423,885 A | 6/1995 | Williams |
| 5,429,638 A | 7/1995 | Muschler et al. |
| 5,439,446 A | 8/1995 | Barry |
| 5,441,515 A | 8/1995 | Khosravi et al. |
| 5,443,500 A | 8/1995 | Sigwart |
| 5,480,400 A | 1/1996 | Berger |
| 5,487,897 A | 1/1996 | Polson et al. |
| 5,496,368 A | 3/1996 | Wiese |
| 5,505,733 A | 4/1996 | Justin et al. |
| 5,511,565 A | 4/1996 | Syers |
| 5,514,137 A | 5/1996 | Coutts |
| 5,536,269 A | 7/1996 | Spievack |
| 5,547,378 A | 8/1996 | Linkow |
| 5,549,676 A | 8/1996 | Johnson |
| 5,549,679 A | 8/1996 | Kuslich |
| 5,562,736 A | 10/1996 | Ray et al. |
| 5,569,308 A | 10/1996 | Sottosanti |
| 5,571,189 A | 11/1996 | Kuslich |
| 5,630,843 A | 5/1997 | Rosenberg |
| 5,655,545 A | 8/1997 | Johnson et al. |
| 5,674,295 A | 10/1997 | Ray et al. |
| 5,676,664 A | 10/1997 | Allard et al. |
| 5,681,309 A | 10/1997 | Ross, Jr. et al. |
| 5,685,716 A | 11/1997 | Linkow |
| 5,695,338 A | 12/1997 | Robert |
| 5,700,479 A | 12/1997 | Lundgren |
| 5,704,939 A | 1/1998 | Justin |
| 5,711,315 A | 1/1998 | Jerusalmy |
| 5,741,223 A | 4/1998 | Janzen et al. |
| 5,746,762 A | 5/1998 | Bass |
| 5,766,173 A | 6/1998 | Ross, Jr. et al. |
| 5,769,856 A | 6/1998 | Dong et al. |
| 5,772,661 A | 6/1998 | Michelson |
| 5,779,728 A | 7/1998 | Lunsford et al. |
| 5,792,400 A | 8/1998 | Talja et al. |
| 5,807,382 A | 9/1998 | Chin |
| 5,810,812 A | 9/1998 | Chin |
| 5,827,289 A | 10/1998 | Reiley et al. |
| 5,839,899 A | 11/1998 | Robinson |
| 5,857,998 A | 1/1999 | Barry |
| 5,873,715 A | 2/1999 | Liou |
| 5,882,353 A | 3/1999 | VanBeek et al. |
| 5,895,387 A | 4/1999 | Guerrero et al. |
| 5,902,304 A | 5/1999 | Walker et al. |
| 5,919,234 A | 7/1999 | Lemperle et al. |
| 5,935,594 A | 8/1999 | Ringeisen et al. |
| 5,941,910 A | 8/1999 | Schindler et al. |
| 5,957,953 A | 9/1999 | DiPoto et al. |
| 5,968,043 A | 10/1999 | Ross, Jr. et al. |
| 5,976,142 A | 11/1999 | Chin |
| 5,977,431 A | 11/1999 | Knapp et al. |
| 5,980,252 A | 11/1999 | Samchukov et al. |
| 5,980,522 A | 11/1999 | Koros et al. |
| 5,990,382 A | 11/1999 | Fox |
| 5,964,767 A | 12/1999 | Tapia et al. |
| 5,997,520 A | 12/1999 | Ahr et al. |
| 6,018,094 A | 1/2000 | Fox |
| 6,019,764 A | 2/2000 | Bartee |
| 6,027,744 A | 2/2000 | Vacanti et al. |
| 6,030,218 A | 2/2000 | Robinson |
| 6,033,412 A | 3/2000 | Losken et al. |
| 6,037,384 A | 3/2000 | Kakizawa |
| 6,042,596 A | 3/2000 | Bonutti |
| 6,045,497 A | 4/2000 | Schweich et al. |
| 6,050,819 A | 4/2000 | Robinson |
| 6,113,599 A | 9/2000 | Landsberger |
| 6,126,660 A | 10/2000 | Dietz |
| 6,127,597 A | 10/2000 | Beyar et al. |
| 6,206,930 B1 | 3/2001 | Burg et al. |
| 6,210,376 B1 | 4/2001 | Grayson |
| 6,214,012 B1 | 4/2001 | Karpman et al. |
| 6,217,323 B1 | 4/2001 | Liou |
| 6,224,599 B1 | 5/2001 | Baynham |
| 6,251,063 B1 | 6/2001 | Silverman et al. |
| 6,264,695 B1 | 7/2001 | Stoy |
| 6,270,346 B1 | 8/2001 | Grabenhofer et al. |
| 6,280,191 B1 | 8/2001 | Gordon |
| 6,293,947 B1 | 9/2001 | Buchbinder |
| 6,293,960 B1 | 9/2001 | Ken |
| 6,302,687 B1 | 10/2001 | King |
| 6,309,220 B1 | 10/2001 | Gittleman |
| 6,322,566 B1 | 11/2001 | Minoretti et al. |
| 6,358,266 B1 | 3/2002 | Bonutti |
| 6,402,518 B1 | 6/2002 | Ashman |
| 6,409,764 B1 | 6/2002 | White et al. |
| 6,506,214 B1 | 1/2003 | Gross |
| 6,616,698 B2 | 9/2003 | Scarborough |
| 6,740,093 B2 | 4/2004 | Hochschuler et al. |
| 6,758,673 B2 | 7/2004 | Fromovich et al. |
| 7,153,306 B2 | 12/2006 | Ralph |
| 7,244,241 B2 | 7/2007 | Gross |
| 7,396,232 B2 | 7/2008 | Fromovich et al. |
| 7,510,397 B2* | 3/2009 | Hochman ............ A61C 8/0033 433/172 |
| 8,002,548 B2 | 8/2011 | Lee |
| 8,333,589 B2 | 12/2012 | Kfir |
| 8,864,841 B2 | 10/2014 | Karmon |
| 8,882,507 B2 | 11/2014 | Hertz |
| 9,498,308 B1* | 11/2016 | Krastev ............... A61C 8/0092 |
| 9,615,841 B2* | 4/2017 | Eder ................... A61B 17/1688 |

(56) References Cited

U.S. PATENT DOCUMENTS

| | | | |
|---|---|---|---|
| 9,757,215 B2 * | 9/2017 | Song | A61C 8/0092 |
| 9,795,467 B2 * | 10/2017 | Krastev | A61C 8/0092 |
| 10,080,625 B2 * | 9/2018 | Eder | A61C 1/0046 |
| 2001/0012607 A1 | 8/2001 | Robinson | |
| 2002/0094951 A1 | 7/2002 | Horiuchi et al. | |
| 2002/0177102 A1 | 11/2002 | Martin et al. | |
| 2005/0074437 A1 | 4/2005 | Horvath | |
| 2006/0084034 A1 | 4/2006 | Hochman | |
| 2006/0172255 A1 | 8/2006 | Hochman et al. | |
| 2007/0059827 A1 | 3/2007 | Horvath | |
| 2008/0319466 A1 | 12/2008 | Eder | |
| 2009/0181345 A1 * | 7/2009 | Kfir | A61C 8/0092 433/172 |
| 2010/0047733 A1 | 2/2010 | Nahlieli | |
| 2010/0049330 A1 | 2/2010 | Horvath | |
| 2010/0081111 A1 | 4/2010 | Better et al. | |
| 2010/0081112 A1 * | 4/2010 | Better | A61C 8/0039 433/174 |
| 2010/0196841 A1 | 8/2010 | Nahlieli | |
| 2010/0221681 A1 | 9/2010 | Hochman | |
| 2010/0255444 A1 | 10/2010 | Karmon | |
| 2011/0009978 A1 | 1/2011 | Horvath | |
| 2011/0039232 A1 * | 2/2011 | Yu | A61B 17/663 433/173 |
| 2011/0270236 A1 | 11/2011 | Eder | |
| 2012/0171293 A1 | 7/2012 | Horvath | |
| 2013/0261671 A1 | 10/2013 | Horvath | |
| 2013/0261672 A1 | 10/2013 | Horvath | |
| 2013/0274819 A1 | 10/2013 | Horvath | |
| 2014/0005794 A1 | 1/2014 | Horvath | |
| 2014/0038126 A1 | 2/2014 | Krastev | |
| 2014/0105988 A1 | 4/2014 | Horvath | |
| 2015/0320522 A1 * | 11/2015 | Eder | A61C 1/0061 433/173 |

FOREIGN PATENT DOCUMENTS

| | | |
|---|---|---|
| DE | 19803628 A1 | 1/1999 |
| DE | 19907420 A1 | 9/2000 |
| DE | 10036027 A1 | 1/2002 |
| DE | 202006013643 U1 | 2/2008 |
| EP | 0107779 A1 | 5/1984 |
| EP | 0411767 A1 | 2/1991 |
| EP | 1159984 B1 | 12/2001 |
| EP | 1174094 A1 | 1/2002 |
| EP | 2062548 A3 | 5/2009 |
| JP | 2004-518452 C1 | 6/2004 |
| JP | 2006192040 A | 7/2006 |
| JP | 2009-536070 A | 10/2009 |
| JP | 2012-509092 A | 4/2012 |
| KR | 1020110007794 | 1/2011 |
| WO | 1988/01517 | 3/1988 |
| WO | 1993/21858 | 11/1993 |
| WO | 1995/18638 | 7/1995 |
| WO | 1996/13221 | 5/1996 |
| WO | 1996/024310 | 8/1996 |
| WO | 1999/02214 | 1/1999 |
| WO | 200004940 | 2/2000 |
| WO | 2000/21455 | 4/2000 |
| WO | 2001091663 | 12/2001 |
| WO | 2006/096900 | 9/2006 |
| WO | 2007/129312 | 11/2007 |
| WO | 2011132871 A3 | 12/2011 |
| WO | 2014/000007 | 1/2014 |

OTHER PUBLICATIONS

Notice of deficiencies in Israeli patent application No. 243401 from Israeli Patent Office filed on Feb. 16, 2017.
Notice before accepting of Israeli patent application No. 243401 from Israeli Patent Office filed on Aug. 8, 2017.
Communication under Rule 164(2)(a) Epc in European patent application No. 16 825 573.5 from European Patent Office filed on Jun. 21, 2019 (opening letter).
Communication under Rule 164(2)(a) EPC in European patent application No. 16 825 573.5 from European Patent Office filed on Jun. 21, 2019.
Communication under Rule 94(3) EPC in European patent application No. 16 825 573.5 from European Patent Office filed on Dec. 12, 2019 (opening letter).
Communication under Rule 94(3) EPC in European patent application No. 16 825 573.5 from European Patent Office filed on Dec. 12, 2019.
Communication under Rule 94(3) EPC in European patent application No. 16 825 573.5 from European Patent Office filed on Jun. 16, 2019 (opening letter).
Communication under Rule 94(3) EPC in European patent application No. 16 825 573.5 from European Patent Office filed on Jun. 16, 2019.
Notice of Reasons for Refusal of Japanese Patent Application No. 2018-533802 from Japanese Patent Office filed on Oct. 8, 2020.

* cited by examiner

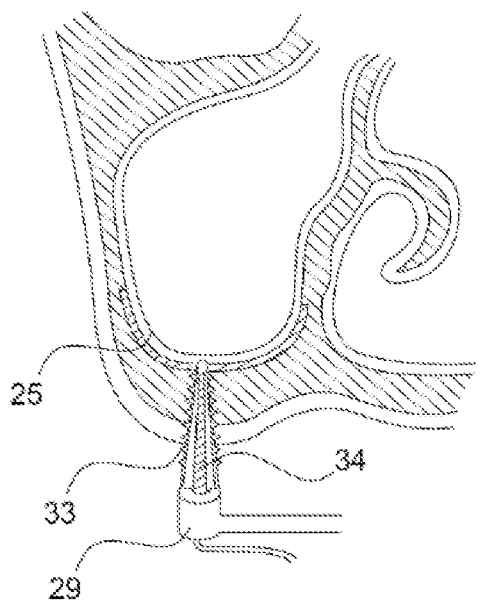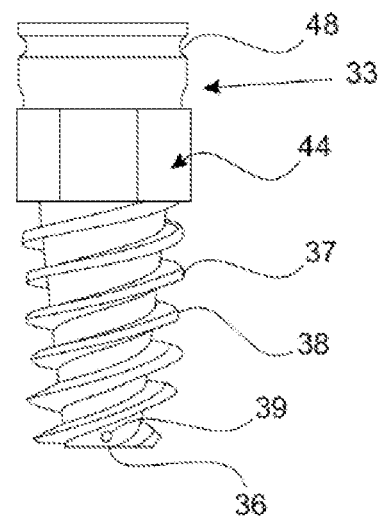
FIG. 5　　　　　FIG. 6
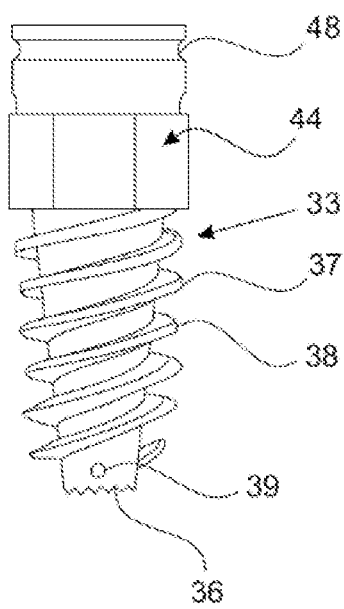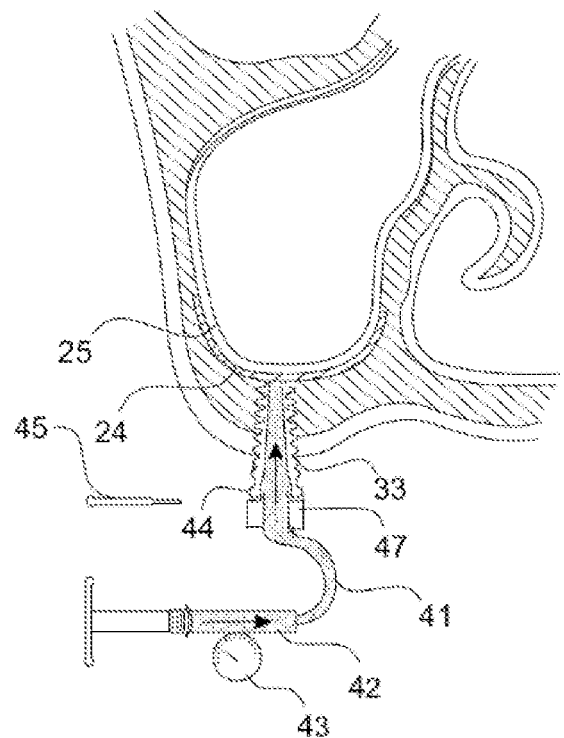
FIG. 7　　　　　FIG. 8

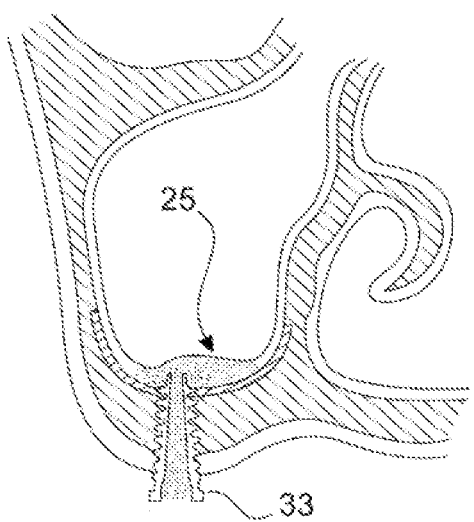
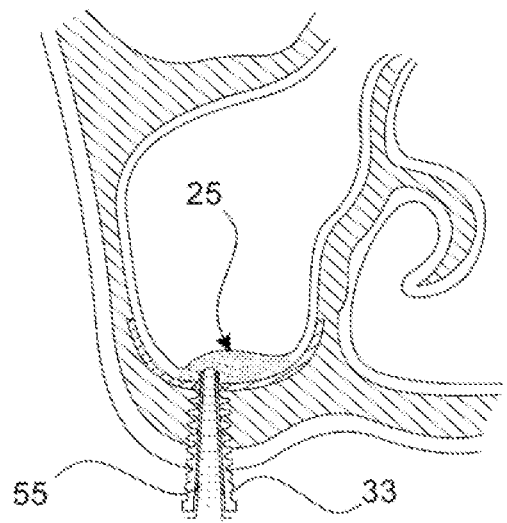
FIG. 13
FIG. 14
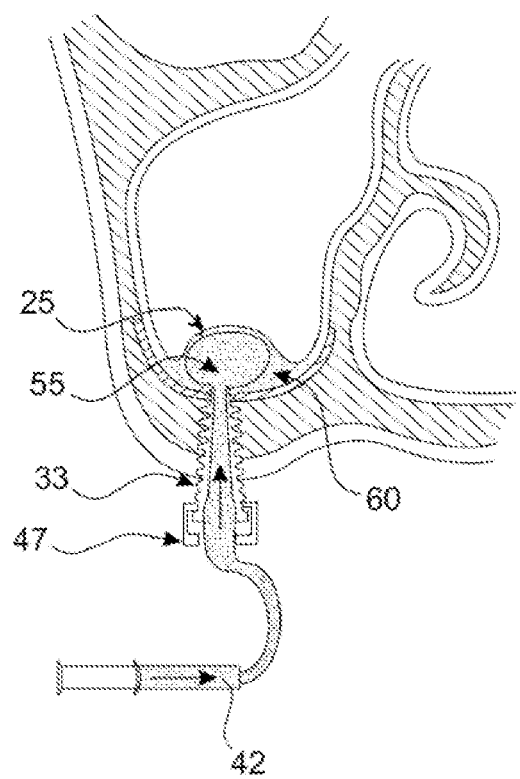
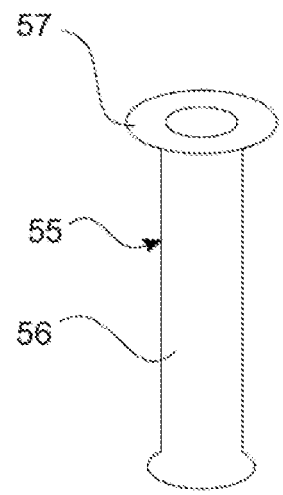
FIG. 15
FIG. 16

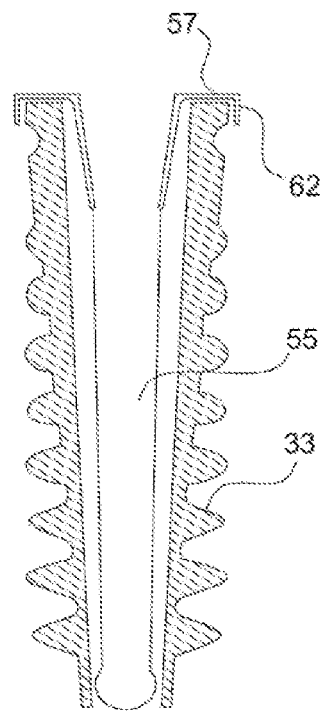
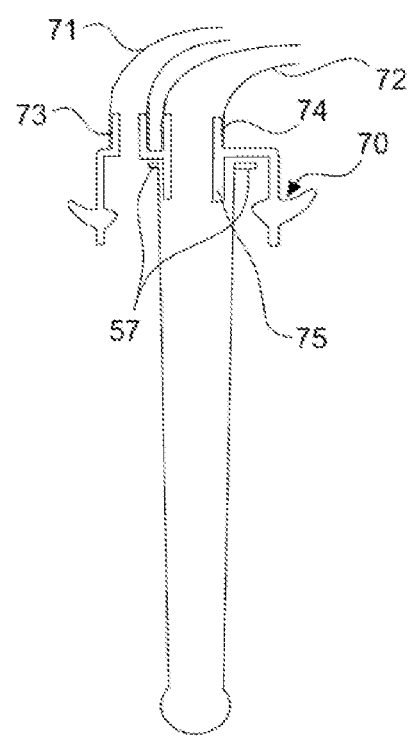
FIG. 21 FIG. 22
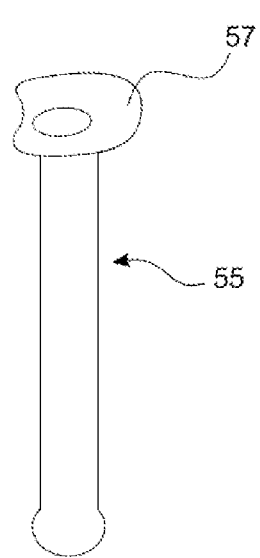
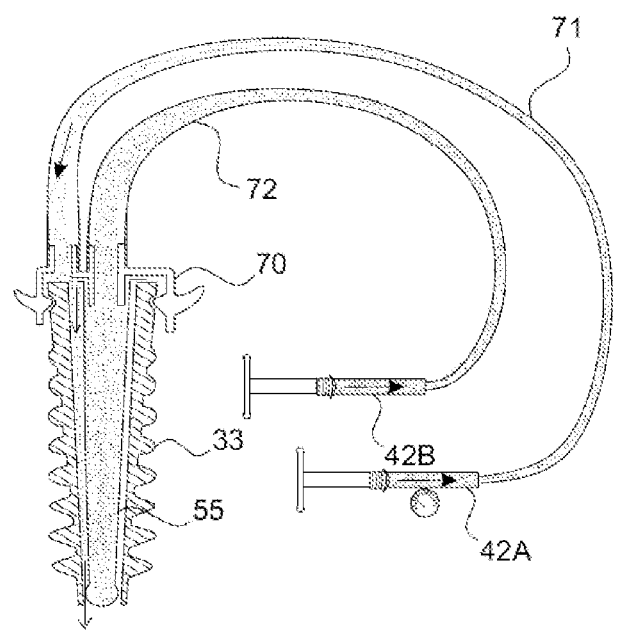
FIG. 23 FIG. 24

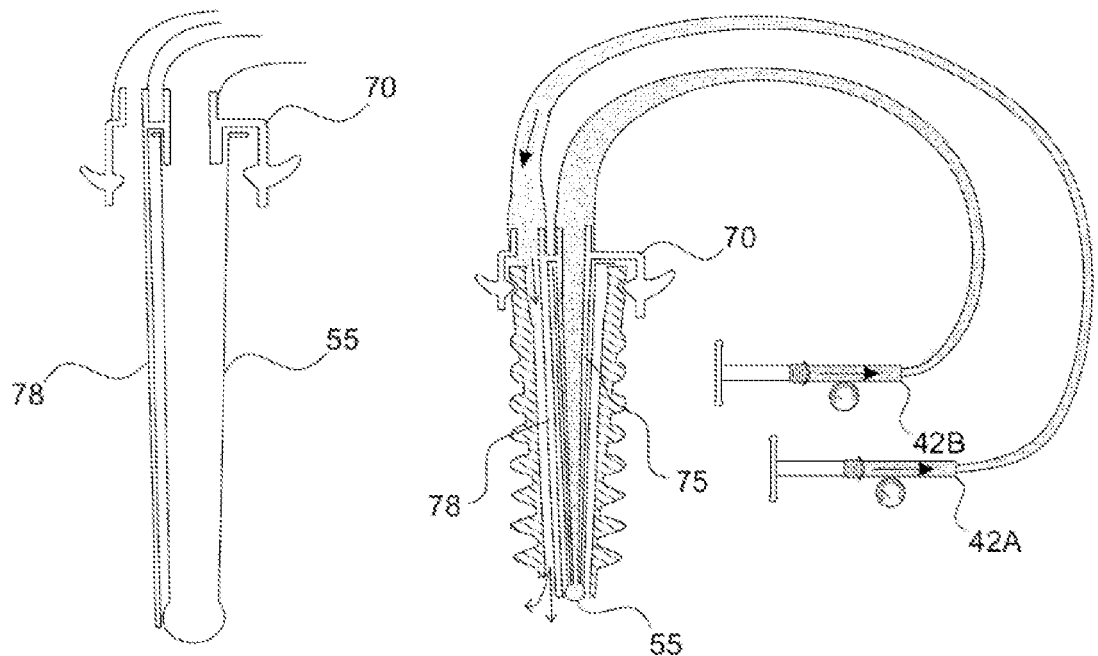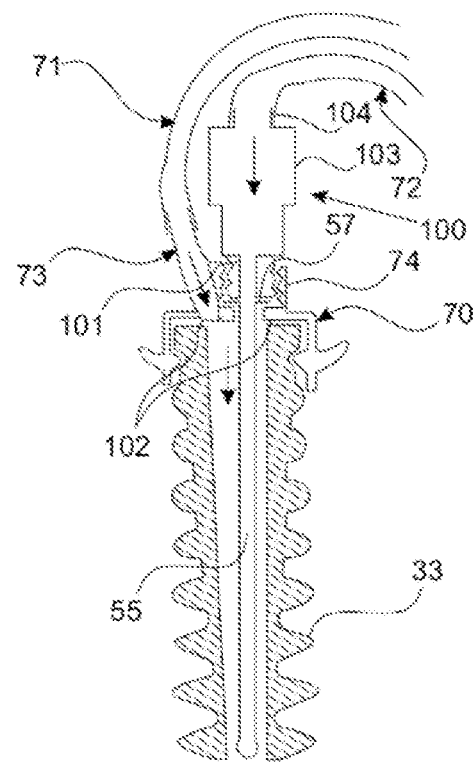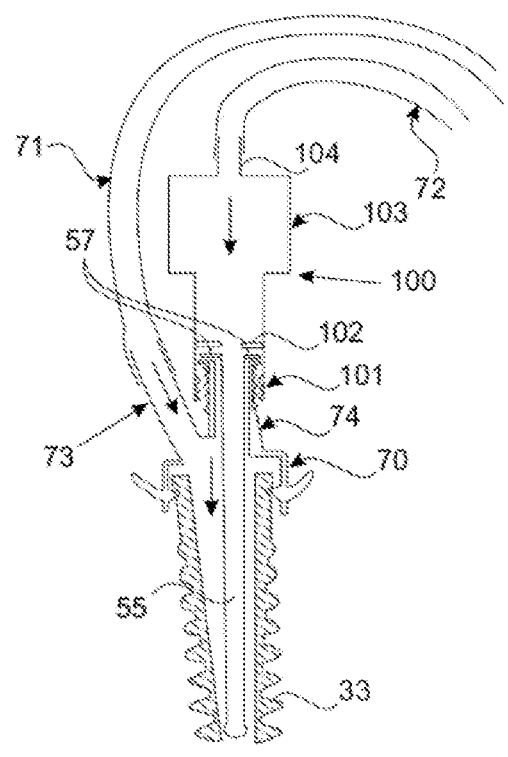
FIG. 27　　FIG. 28
FIG. 29　　FIG. 30

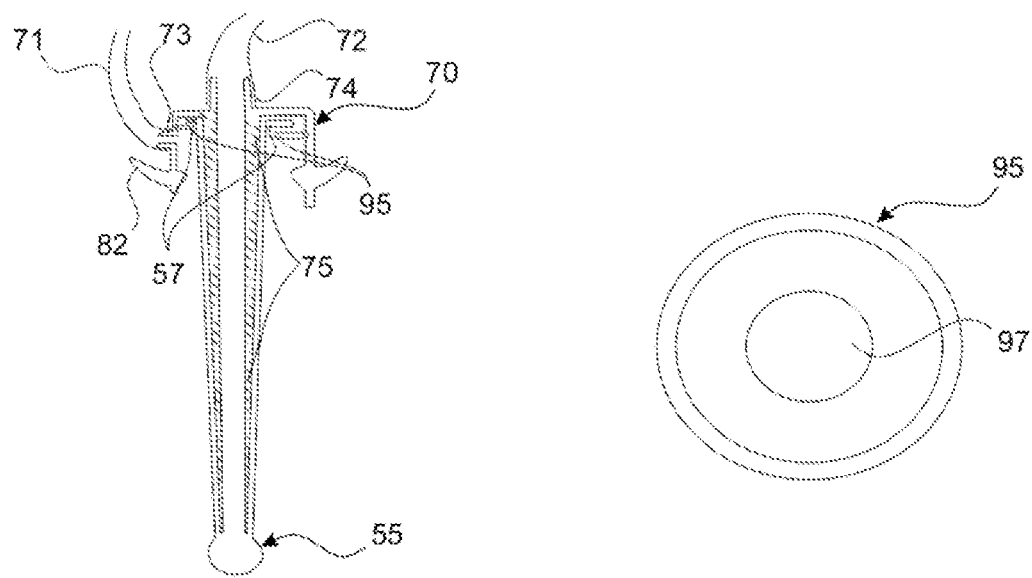
FIG. 35
FIG. 36
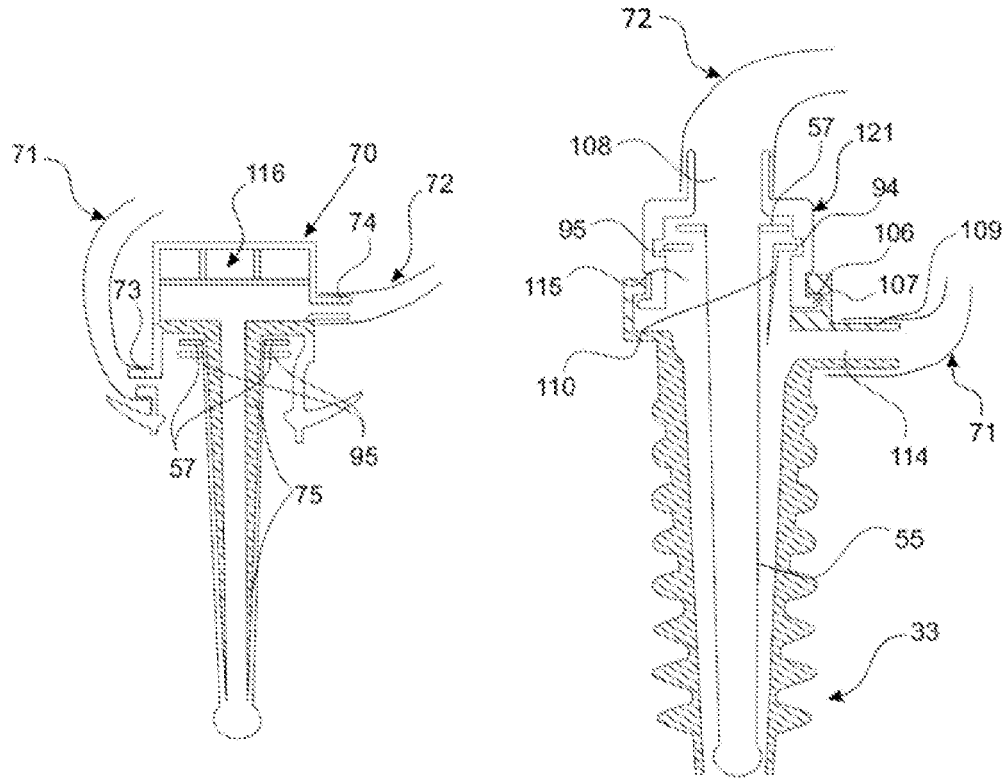
FIG. 37
FIG. 38

DEVICES AND METHODS FOR ELEVATING THE SCHNEIDERIAN MEMBRANE

FIELD AND BACKGROUND OF THE INVENTION

The present invention relates to an improved devices and methods for elevating the Schneiderian membrane which is also called a "sinus lift" in a safe and reliable manner.

In cases when there is not enough bone below the maxillary sinus to enable the insertion of long enough dental implants a procedure of augmenting bone inside the maxillary sinus can be performed. This procedure is called sinus lift or subantral augmentation. This procedure can be done before the insertion of the dental implants so the dental implants are inserted several months after performing the sinus lift. Another option is to insert the implants during performing the sinus lift procedure or immediately after, provided the dental implants can be stabilized by the alveolar ridge bone below the maxillary sinus. There are several methods to perform this augmentation of the maxillary sinus:

The sinus lift technique introduced by Dr. Tatum:

This procedure which is also called "open sinus lift" is the most popular. It requires cutting a "trapdoor" in the lateral wall of the maxillary sinus and then lifting gently the Schneiderian membrane without tearing the membrane, then placing bone craft materials beneath the lifted membrane, then covering the "trapdoor" with a membrane and suturing. This technique has some drawbacks:

1. It is a relative big operation.
2. The technique is complicated.
3. The Schneiderian membrane can be easily torn which increases the risk for infection of the maxillary sinus and failure of the operation.

The sinus lift technique introduced by Dr. Summers:

This technique which is also called "closed sinus lift", requires breaking the floor of the maxillary sinus after penetrating through the alveolar ridge bone beneath the maxillary sinus. The bone graft is pushed into the penetration in the alveolar ridge bone and therefore the Schneiderian membrane is elevated. This procedure has advantage over the Tatum's technique that the procedure is simpler and the operation is smaller, bat has also drawbacks:

1. The amount of augmentation is limited.
2. The Schneiderian membrane can be torn without the awareness of the surgeon, resulting in filling the graft material above the Schneiderian membrane and failure of the procedure.

The hydraulic and balloon sinus lift techniques introduced by Karmon (U.S. Pat. No. 8,864,841):

In the pure hydraulic technique a flowable material is injected below the Schneiderian membrane causing the Schneiderian membrane to be elevated. The flowable material can be for example saline or a flowable bone augmenting material. This procedure has advantage over the Summers' technique so the risk of tearing the Schneiderian membrane is smaller since the pressure on the Schneiderian membrane is better distributed, according Pascal's rule. An even distribution of pressure on the Schneiderian membrane allows for higher elevation of the Schneiderian membrane. This procedure can be done with a cannula or with a hollow dental implant. However this procedure has also drawbacks:

1) The Schneiderian membrane can be torn during preparing the opening in the floor of the maxillary sinus.
2) There is no control where the Schneiderian membrane will be elevated. The Schneiderian membrane will be elevated where its attachment to the floor of the maxillary sinus is the weakest and not necessarily where the dental implants are going to be inserted.
3) The amount of bone augmentation material needed is significantly higher. This is because, sometimes, instead of having a large elevation of the Schneiderian membrane in a specific small area, the result is a low elevation along a large area. Therefore a large amount of bone augmentation material is required to reach the desired elevation in the required location.
3) In case there is even a very small tear in the Schneiderian membrane the procedure can't be used.

In the balloon sinus lift technique of Karmon the flowable material is introduced inside a balloon or an expandable container so when the balloon is expanded the Schneiderian membrane is elevated. In this technique the place of elevating the Schneiderian membrane and the amount of elevation are controlled and if small tears in the Schneiderian membrane occur, sometimes the balloon itself can close these small tears and the procedure can be continued. Using the balloon allows for better distribution of the forces along the Schneiderian membrane than the distribution of the forces using the Summers' technique, therefore allowing for safer and higher elevation of the Schneiderian membrane. However this procedure has also drawbacks: The distribution of the forces using the balloon is not as good compared to the pure hydraulic technique without the balloon. In the balloon technique the balloon is touching only part of the Schneiderian membrane and there is no even distribution of forces. Some regions of the Schneiderian membrane are exposed to stronger forces which can lead to tearing of the Schneiderian membrane. When comparing the balloon technique to the pure hydraulic technique without the balloon, the balloon technique allows for better control on the location and amount of the elevation of the Schneiderian membrane, but has higher risk of tearing the membrane compared to the pure hydraulic method.

The sinus lift procedure can be divided to two stages—the first stage of perforating gently the floor or the lateral wall of the maxillary sinus and a second stage of elevating the Schneiderian membrane through this perforation. The hydraulic and balloon methods are dealing mainly with the second stage of elevating the Schneiderian membrane. There are also devices to reduce the risk of perforating the Schneiderian membrane during perforating the floor or the lateral wall of the maxillary sinus, like special drills and piezosurgery tips. However these devices require high skills of the dentist and perforations of the Schneiderian membrane occur.

Therefore there is a need for better devices and methods that will allow safer perforation of the floor of the maxillary sinus and controlled and safe elevation of the Schneiderian membrane, using a minimally invasive technique.

SUMMARY OF THE INVENTION

The present invention provides devices and methods to perform a minimally invasive, controlled and safe sinus lift. In one embodiment of the present invention:

1) a cannula is inserted through the alveolar ridge bone below the Schneiderian membrane of the maxillary sinus.
2) A flowable material is injected through this cannula to elevate the Schneiderian membrane.
3) A balloon which can be located inside this cannula is expanded inside the maxillary sinus below the Schneiderian membrane, while the flowable material is still inside the maxillary sinus to elevate the Schneiderian membrane while pushing also the flowable material inside the maxillary sinus around the balloon.

The simultaneous pressure over the Schneiderian membrane by the balloon itself and by the surrounding flowable material around the balloon allows for better distribution of the forces along the Schneiderian membrane. Now, in addition to the balloon pushing the Schneiderian membrane, the flowable material around the balloon is also pushing and elevating the Schneiderian membrane therefore the risk for tearing of the Schneiderian membrane is reduced. In this combined technique of using a pure hydraulic technique with a balloon technique, a synergistic effect is achieved so the expansion of the balloon is producing in addition to the balloon itself an additional hydraulic pressure so the distribution of the forces along the Schneiderian membrane is more even and becomes more close to the distribution according to Pascal's rule. This synergistic effect allows for better distribution of the forces resulting in reduced risk of tearing the Schneiderian membrane while controlling the location of the elevation of the Schneiderian membrane which is dictated mainly by the balloon.

Other objects and features of the present invention will become apparent in the following detailed description when taken in connection with the accompanying drawings which disclose several embodiments of the invention. It is to be understood that the drawings are designed for the purpose of illustration only and are not intended as a definition of the limits of the invention.

It is also to be understood that any combination of the embodiments described hereafter can be used although these combinations are not explicitly described The number of possible combinations of different elements in different relations to each other and the number of options of using the devices is enormous. Therefore only several embodiments are described and illustrated.

Thus, according to the teachings of the present invention there is provided a device for elevating the Schneiderian membrane of the maxillary sinus to treat the majority of human patients in need for enlargement of the height of a maxillary alveolar ridge bone comprising:

a cannula for insertion through an opening in a human maxillary alveolar ridge bone towards the Schneiderian membrane and a balloon, the cannula being sized to be inside the maxillary alveolar ridges of the majority of human patients in need for enlargement of the height of the maxillary alveolar ridge bone, the cannula has an external thread to be engaged with the bony walls of the maxillary alveolar ridge bone below the Schneiderian membrane, at least part of the balloon being inside the cannula, a proximal part of the cannula being connected to a first filling tube so when advancing a first liquid though the first filling tube the first liquid pass through the cannula inside the maxillary sinus to elevate the Schneiderian membrane, the proximal part of the cannula being connected to a second filling tube so when advancing a second liquid though the second filling tube, the second liquid being inserted inside the balloon so as to expand at least part of the balloon inside the maxillary sinus to elevate the Schneiderian membrane.

According to a further feature of the present invention, at least one the filling tubes being connected to the cannula by a connector.

According to a further feature of the present invention, the at least part of the balloon being advanced from inside the cannula to outside the cannula through the distal end of the cannula to be expanded along the central longitudinal axis of the cannula while being fixated to the cannula.

According to a further feature of the present invention, the first filling tube and the second filling tube being connected to the cannula by the same connector.

According to a further feature of the present invention, the first filling tube being connected to a first injecting element.

According to a further feature of the present invention, the second filling tube being connected to a second injecting element.

According to a further feature of the present invention, at least one of the injecting elements has a pressure measuring device.

According to a further feature of the present invention, at least one of the injecting elements has a piston which can be advanced by screwing.

According to a further feature of the present invention, the first liquid is passing between the balloon and the inner wall of the cannula while touching the inner wall.

According to a further feature of the present invention, the first liquid being laterally to the periphery of the balloon inside the cannula during the advancing of the first liquid.

According to a further feature of the present invention, the first liquid surrounds at least the majority of the balloon inside the cannula during the advancing of the first liquid.

According to a further feature of the present invention, the balloon has an elongated body and a base, the length of the elongated body of the balloon is 2 mm-30 mm, the external diameter of the elongated body of the balloon is 1-4 mm, the base of the balloon being wider than the elongated body of the balloon.

According to a further feature of the present invention, the external diameter of the distal end of the cannula is 2-5.5 mm.

According to a further feature of the present invention, the external diameter of the distal end of the cannula is 2.5-4.7 mm.

According to a further feature of the present invention, the external diameter of the distal end of the cannula is 3-4 mm.

According to a further feature of the present invention, the largest external diameter of the most distal 3 mm of the cannula is 2-5.5 mm.

According to a further feature of the present invention, the largest external diameter of the most distal 3 mm of the cannula is 2.5-4.7 mm.

According to a further feature of the present invention, the largest external diameter of the most distal 3 mm of the cannula is 3-4 mm.

According to a further feature of the present invention, the length of the cannula is 6-25 mm.

According to a further feature of the present invention, the length of the cannula is 8-20 mm.

According to a further feature of the present invention, the length of the cannula is 10-18 mm.

According to a further feature of the present invention, the external thread of the cannula extends along 5-20 mm.

According to a further feature of the present invention, the external thread of the cannula extends along 8-15 mm.

According to a further feature of the present invention, the external thread of the cannula extends along 10-13 mm.

According to a further feature of the present invention, the connector being connected to the cannula by friction.

According to a further feature of the present invention, the connector being connected to the cannula by screwed connection.

According to a further feature of the present invention, the connector being connected to the cannula by a snap connection.

According to a further feature of the present invention, the filling tube continues inside the cannula.

According to a further feature of the present invention, the cannula has an internal anti-rotational element.

According to a further feature of the present invention, the cannula has an external anti-rotational element.

According to a further feature of the present invention, the device further includes a tool to be connected to the cannula from the side to enable rotating the cannula.

According to a further feature of the present invention, the connector has an anti-rotational element and the device further includes a tool to be connected to the connector to enable rotating the connector and the cannula.

According to a further feature of the present invention, the cannula has a slot at its proximal part and the connector has a flexible distal extension that can be inserted inside the slot after being bended to enable a detachable connection to the connector.

According to a further feature of the present invention, the balloon being fixated to the connector a by a fixating ring.

According to a further feature of the present invention, the balloon has a wider base, the wider base has a noncircular shape.

According to a further feature of the present invention, the balloon has a wider base, the wider base has a hole to allow the passage of the first liquid.

According to a further feature of the present invention, the balloon has a wider base, the wider base being outside the cannula.

According to a further feature of the present invention, the balloon has a wider base, the wider base being inside the cannula.

According to a further feature of the present invention, the cannula has a first internal channel and a second internal channel, the first liquid being advanced from the first filling tube to pass through the first internal channel of the cannula, at least part of the balloon being inside the second internal channel of the cannula.

According to a further feature of the present invention, the distal end of the external wall of the first internal channel of the cannula being located proximally to the distal end of the internal wall of the first internal channel of the cannula.

According to a further feature of the present invention, a proximal part of the cannula has a non-circular configuration to allow connection to the connector in a predetermined relation.

According to a further feature of the present invention, the connector includes an elongated projection to be inserted inside the cannula adjacent the balloon and displaced from the internal wall of the cannula.

According to a further feature of the present invention, the distal end of the elongated projection being adjacent the distal end of the cannula.

According to a further feature of the present invention, the cannula has an opening at a side wall of the cannula adjacent the distal end of the cannula.

According to a further feature of the present invention, the connector has a distally protruding tube protruding distally inside the balloon.

According to a further feature of the present invention, the distal end of the distally protruding tube being adjacent the distal end of the cannula.

According to a further feature of the present invention, the balloon being fixated to the connector.

According to a further feature of the present invention, the balloon being glued to the connector.

According to a further feature of the present invention, the connector has a slot and the balloon being fixated to the connector by a fixating ring having flexible border inside the slot of the connector.

According to a further feature of the present invention, the connector has a thread and the balloon being fixated to the connector by a fixating ring being screwed to the connector.

According to a further feature of the present invention, the connector connects the second filling tube to the cannula, so when a distal part of the connector being screwed to the cannula a wider base of the balloon being pressed and fixated.

According to a further feature of the present invention, a secondary connector connects the connector to the second filling tube so when a distal part of the secondary connector being screwed to the connector, a wider base of the balloon being pressed and fixated.

According to a further feature of the present invention, part of the connector being part of the cannula.

According to a further feature of the present invention, the connector being part of the cannula to form one-piece.

According to a further feature of the present invention, the external thread of the cannula doesn't reach the distal end of the cannula.

According to a further feature of the present invention, the external thread of the cannula reach the distal end of the cannula.

According to a further feature of the present invention, the first liquid includes materials that promote bone growth.

According to a further feature of the present invention, the first liquid being different from the second liquid.

According to a further feature of the present invention, the external thread of the cannula has two external threads each external thread has a thread pitch of 1.5-2.5 mm.

According to a further feature of the present invention, the largest external diameter of the intra-bony part of the cannula is 2.5-4.5 mm.

According to a further feature of the present invention, the largest internal diameter of the intra-bony part of the cannula is 1-3.5 mm.

According to a further feature of the present invention, the balloon has an elongated body and a wider base, the external diameter of the elongated body is 1.0-3.5 mm, the external diameter of the wider base is 2-6 mm.

Thus, according to the teachings of the present invention there is provided a system for elevating the Schneiderian membrane of the maxillary sinus to treat the majority of human patients in need for enlargement of the height of a maxillary alveolar ridge bone comprising:

an osteotome for insertion through a human maxillary alveolar ridge bone towards the Schneiderian membrane, a mallet, a first injecting element and a first filling tube, the osteotome being sized to be inside the maxillary alveolar ridges of the majority of human patients in need for enlargement of the height of the maxillary alveolar ridge bone, the ostetome includes a distal opening at a distal end of the osteotome, the osteotome includes a proximal opening proximally to the distal opening, the osteotome includes an internal channel extending from the proximal opening to the distal opening, a proximal part of the first filling tube being connected to the first injecting element which includes a first liquid, a distal part of the first filling tube being connected to the internal channel so when the first injecting element being activated the first liquid being pressurized inside the osteotome, the mallet being designed to apply force to a proximal part of the osteotome so the distal end of the osteotomy will break the floor of the maxillary sinus to enable the pressurized first liquid to advance from inside the internal channel through the break to below the Schneiderian membrane to elevate the Schneiderian membrane.

According to a further feature of the present invention, the first filling tube being connected to the osteotome by a connector.

According to a further feature of the present invention, the mallet being activated by a machine.

According to a further feature of the present invention, the mallet being a magnetic mallet.

According to a further feature of the present invention, the first injecting element and the mallet are part of the same device.

According to a further feature of the present invention, the internal channel doesn't reach the proximal part of the osteotome.

According to a further feature of the present invention, the osteotome being bended at least in one location.

According to a further feature of the present invention, the first filling tube being connected to the osteotome by a first connector.

According to a further feature of the present invention, the injecting elements has a pressure measuring system.

According to a further feature of the present invention, the first injecting elements has a piston which can be advanced by screwing.

According to a further feature of the present invention, the external diameter of the distal end of the osteotome is 1-5.5 mm.

According to a further feature of the present invention, the external diameter of the distal end of the osteotome is 2-4.7 mm.

According to a further feature of the present invention, the external diameter of the distal end of the osteotome is 3-4 mm.

According to a further feature of the present invention, the largest external diameter of the most distal 3 mm of the osteotome is 1.5-5.5 mm.

According to a further feature of the present invention, the largest external diameter of the most distal 3 mm of the osteotome is 2.5-4.7 mm.

According to a further feature of the present invention, the largest external diameter of the most distal 3 mm of the osteotome is 3-4 mm.

According to a further feature of the present invention, the connector being connected to the osteotome by friction.

According to a further feature of the present invention, the connector being connected to the osteotome by a screwed connection.

According to a further feature of the present invention, the connector being connected to the osteotome by a snap connection.

According to a further feature of the present invention, the connector has a clip to enable an easy detachment of the connector from the osteotome.

According to a further feature of the present invention, the osteotome has a slot inside the internal channel and the connector has a flexible distal extension that can be inserted inside the slot after being bended to enable a detachable connection to the connector.

According to a further feature of the present invention, the osteotome has an opening at a side wall of the osteotome adjacent the distal end of the osteotome.

According to a further feature of the present invention, part of the connector being part of the osteotome.

According to a further feature of the present invention, the connector being part of the osteotome to form one-piece.

According to a further feature of the present invention, the first liquid includes materials that promote bone growth.

According to a further feature of the present invention, the system further includes a balloon located inside the internal channel, the balloon being connected to a second injecting element having a second liquid by a second filling tube so when the injecting element being activated at least part of the balloon being expanded and advanced distally to the distal end of the osteotome along the central longitudinal axis of the distal part of the osteotome.

According to a further feature of the present invention, the second filling tubes being connected to the osteotome by a connector.

According to a further feature of the present invention, the first filling tube and the second filling tube being connected to the osteotome by the same connector.

According to a further feature of the present invention, at least one of the injecting elements has a pressure measuring system.

According to a further feature of the present invention, at least one of the injecting elements has a piston which can be advanced by screwing.

According to a further feature of the present invention, the first liquid being advanced between the balloon and the inner wall of the internal channel while touching the inner wall.

According to a further feature of the present invention, the first liquid being laterally to the periphery of the balloon inside the osteotome during the advancement of the first liquid.

According to a further feature of the present invention, the first liquid surrounds at least the majority of the balloon inside the osteotome during the advancement of the first liquid.

According to a further feature of the present invention, the balloon has an elongated body and a base, the length of the elongated body of the balloon is 2 mm-20 mm, the external diameter of the elongated body of the balloon is 1-4 mm, the base being wider than the elongated body.

According to a further feature of the present invention, the balloon has an elongated body and a wider base, the wider base being located proximally to the elongated body.

According to a further feature of the present invention, the balloon being fixated to the connector a by a fixating ring.

According to a further feature of the present invention, the balloon has a wider base, the wider base has a hole to allow the passage of the first liquid.

According to a further feature of the present invention, the balloon has a wider base, the wider base being outside the osteotome.

According to a further feature of the present invention, the balloon has a wider base, the wider base being inside the osteotome.

According to a further feature of the present invention, the balloon being fixated to the connector.

According to a further feature of the present invention, the connector has a slot and the balloon being fixated to the connector by a fixating ring having flexible border inside the slot of the connector.

According to a further feature of the present invention, the connector has a thread and the balloon being fixated to the connector by a fixating ring being screwed to the connector.

According to a further feature of the present invention, the first liquid being different from the second liquid.

According to a further feature of the present invention, the balloon has an elongated body and a wider base, the external diameter of the elongated body is 1.0-3.5 mm, the external diameter of the wider base is 2-6 mm.

Thus, according to the teachings of the present invention there is provided a method for displacing the Schneiderian membrane comprising:

a) performing a path of insertion through the maxillary alveolar ridge bone towards the Schneiderian membrane;

b) performing a perforation in the floor of the maxillary sinus while preserving the integrity of the Schneiderian membrane;

b) inserting through the perforation a liquid to be between the floor of the maxillary sinus and the Schneiderian membrane so as to elevate the Schneiderian membrane;

d) expanding at least part of a balloon between the floor of the maxillary sinus and the Schneiderian membrane while the balloon is in contact with the liquid and the liquid is prevented from leaking out through the path of insertion so as to further elevate the Schneiderian membrane.

According to a further feature of the present invention, the liquid being inserted through a cannula which is inserted inside the path of insertion.

According to a further feature of the present invention, the balloon being inserted through the cannula.

According to a further feature of the present invention, the perforation in the floor of the maxillary sinus is performed by drilling with a drill through the cannula.

According to a further feature of the present invention, the cannula has an external thread and an anti-rotational element to enable screwing the cannula inside the path of insertion.

According to a further feature of the present invention, the drill being rotated by a handpiece, the handpiece is touching the cannula so the drill is prevented from drilling more than 1 mm distally to the distal end of the cannula.

According to a further feature of the present invention, drilling is done in more than one step so in each step the cannula being inserted deeper inside the alveolar ridge bone.

According to a further feature of the present invention, a flowable bone augmenting material is inserted through the cannula between the floor of the maxillary sinus and the Schneiderian membrane after being elevated.

According to a further feature of the present invention, before the expansion of the balloon a distal end of the cannula being located above the floor of the maxillary sinus.

According to a further feature of the present invention, the cannula being connected to a distal end of a filling tube in a detachable manner without rotating the filling tube relatively to the cannula, a proximal end of the filling tube being connected to an injecting element having the liquid.

According to a further feature of the present invention, the balloon has an elongated body and a base, the length of the elongated body of the balloon is 5 mm-20 mm, the external diameter of the elongated body of the balloon is 1-4 mm, the base being wider than the elongated body.

According to a further feature of the present invention, the cannula has a first channel and a second channel, the liquid being inserted through the first channel, the balloon being inside the second channel.

According to a further feature of the present invention, the second channel being wider than the first channel.

According to a further feature of the present invention, the cannula being connected to a second filling tube, the second filling tube being connected to a second injecting element having a second liquid.

According to a further feature of the present invention, the distal opening of the second channel being located distally to the distal opening of the first channel.

According to a further feature of the present invention, the first channel has a second opening at a side wall of the first channel adjacent the distal opening of the first channel.

According to a further feature of the present invention, a distally protruding tube being inside the balloon so the connection between the distally protruding tube and the balloon being watertight.

According to a further feature of the present invention, the distal opening of the first channel being located above the floor of the maxillary sinus.

According to a further feature of the present invention, the injecting element and the second injecting element are activated simultaneously.

According to a further feature of the present invention, the cannula being rotated by a tool connected from the buccal side to the cannula.

According to a further feature of the present invention, at least one of the injecting elements has a pressure measuring device.

According to a further feature of the present invention the at least part of the balloon being expanded and advanced distally to the distal end of the cannula along the central longitudinal axis of the cannula.

According to a further feature of the present invention at least one of the injecting elements has a piston which can be advanced by screwing.

According to a further feature of the present invention the first flowable material is passing between the balloon and the inner wall of the cannula while touching the inner wall.

According to a further feature of the present invention the liquid being laterally to the periphery of the balloon inside the cannula during the advancing of the liquid.

According to a further feature of the present invention the liquid surrounds at least the majority the balloon inside the cannula during the advancing of the liquid.

According to a further feature of the present invention, the balloon has an elongated body and a base, the length of the elongated body of the balloon is 2 mm-20 mm, the external diameter of the elongated body of the balloon is 1-4 mm, the base being wider than the elongated body.

According to a further feature of the present invention, the external diameter of the distal end of the cannula is 2-5.5 mm.

According to a further feature of the present invention, the external diameter of the distal end of the cannula is 2.5-4.7 mm.

According to a further feature of the present invention, the external diameter of the distal end of the cannula is 3-4 mm.

According to a further feature of the present invention, the largest external diameter of the most distal 3 mm of the cannula is 2-5.5 mm.

According to a further feature of the present invention, the largest external diameter of the most distal 3 mm of the cannula is 2.5-4.7 mm.

According to a further feature of the present invention, the largest external diameter of the most distal 3 mm of the cannula is 3-4 mm.

According to a further feature of the present invention the length of the cannula is 6-25 mm.

According to a further feature of the present invention the length of the cannula is 8-20 mm.

According to a further feature of the present invention the length of the cannula is 10-18 mm.

According to a further feature of the present invention the external thread of the cannula extends along 5-20 mm.

According to a further feature of the present invention the external thread of the cannula extends along 8-15 mm.

According to a further feature of the present invention the external thread of the cannula extends along 10-13 mm.

Thus, according to the teachings of the present invention there is also provided a method for perforating the floor of a human maxillary sinus without perforating the Schneiderian membrane covering the floor of the maxillary sinus comprising:

a) performing a path of insertion through the maxillary alveolar ridge bone towards the floor of the maxillary sinus;

b) screwing inside the path of insertion a cannula having an external thread so a distal end of the cannula will be adjacent the floor of the maxillary sinus; a proximal part of a filling tube being connected to an injecting element which includes a liquid, a distal part of the filling tube being connected to the cannula;

c) activating the injecting element so the liquid being pressurized inside the cannula;

d) advancing further the cannula until the floor of the maxillary sinus being perforated to enable the pressurized liquid to advance from inside the cannula through the perforation to below the Schneiderian membrane to elevate the Schneiderian membrane.

According to a further feature of the present invention, the cannula has an anti-rotational element to enable screwing the cannula inside the path of insertion.

According to a further feature of the present invention, the path of insertion extends up to 1 mm from the Schneiderian membrane.

According to a further feature of the present invention, before the activation of the injecting elements drilling with a drill through the cannula.

According to a further feature of the present invention, the drill being rotated by a handpiece, the handpiece is touching the cannula so the drill is prevented from drilling more than 1 mm distally to the distal end of the cannula.

According to a further feature of the present invention, drilling is done in more than one step so in each step the cannula being inserted deeper inside the alveolar ridge bone.

According to a further feature of the present invention, a flowable bone augmenting material is inserted through the cannula between the floor of the maxillary sinus and the Schneiderian membrane after being elevated.

According to a further feature of the present invention, the cannula being connected to a distal end of a filling tube in a detachable manner without rotating the filling tube relatively to the cannula, a proximal end of the filling tube being connected to an injecting element having the flowable material.

According to a further feature of the present invention, the cannula has a balloon inside.

According to a further feature of the present invention, the cannula has a second opening at a side wall of the cannula adjacent the distal end of the cannula.

According to a further feature of the present invention, the injecting element is a syringe in which the piston being advanced by screwing.

According to a further feature of the present invention, the injecting element has a mechanism to control the pressure inside the cannula.

According to a further feature of the present invention, the cannula being rotated by a tool connected from the buccal side to the cannula.

According to a further feature of the present invention, at least one of the injecting elements has a pressure measuring device.

According to a further feature of the present invention the at least part of the balloon being expanded and advanced distally to the distal end of the cannula along the central longitudinal axis of the cannula.

According to a further feature of the present invention at least one of the injecting elements has a piston which can be advanced by screwing.

According to a further feature of the present invention the liquid is passing between the balloon and the inner wall of the cannula while touching the inner wall.

According to a further feature of the present invention the liquid being laterally to the periphery of the balloon inside the cannula during the advancing of the liquid.

According to a further feature of the present invention the liquid surrounds at least the majority of the balloon inside the cannula during the advancing of the liquid.

According to a further feature of the present invention, the balloon has an elongated body and a base, the length of the elongated body of the balloon is 2 mm-20 mm, the external diameter of the elongated body of the balloon is 1-4 mm, the base being wider than the elongated body.

According to a further feature of the present invention, the external diameter of the distal end of the cannula is 2-5.5 mm.

According to a further feature of the present invention, the external diameter of the distal end of the cannula is 2.5-4.7 mm.

According to a further feature of the present invention, the external diameter of the distal end of the cannula is 3-4 mm.

According to a further feature of the present invention, the largest external diameter of the most distal 3 mm of the cannula is 2-5.5 mm.

According to a further feature of the present invention, the largest external diameter of the most distal 3 mm of the cannula is 2.5-4.7 mm.

According to a further feature of the present invention, the largest external diameter of the most distal 3 mm of the cannula is 3-4 mm.

According to a further feature of the present invention the length of the cannula is 6-25 mm.

According to a further feature of the present invention the length of the cannula is 8-20 mm.

According to a further feature of the present invention the length of the cannula is 10-18 mm.

According to a further feature of the present invention the external thread of the cannula extends along 5-20 mm.

According to a further feature of the present invention the external thread of the cannula extends along 8-15 mm.

According to a further feature of the present invention the external thread of the cannula extends along 10-13 mm.

Thus, according to the teachings of the present invention there is also provided a method for perforating the floor of a human maxillary sinus without perforating the Schneiderian membrane covering the floor of the maxillary sinus comprising:

a) inserting an osteotome through the maxillary alveolar ridge bone towards the floor of the maxillary sinus so a distal end of the cannula will be adjacent the floor of the maxillary sinus, the ostetome includes a distal opening at a distal end of the osteotome, the osteotome includes a proximal opening proximally to the distal opening, the osteotome includes an internal channel extending from the proximal opening to the distal opening, a proximal part of a filling tube being connected to an injecting element which includes a liquid, a distal part of the filling tube being connected to the internal channel;

b) activating the injecting element so the liquid being pressurized inside the osteotome;

c) activating the mallet to apply force to a proximal part of the osteotome so the distal end of the osteotomy will break the floor of the maxillary sinus to enable the pressurized liquid to advance from inside the internal channel through the break to below the Schneiderian membrane to elevate the Schneiderian membrane.

Other features of the present invention are the same as for the previous invention and as for the following invention.

Thus, according to the teachings of the present invention there is also provided a device for elevating the Schneiderian membrane of the maxillary sinus to treat normal human patients in need for enlargement of the height of a maxillary alveolar ridge bone comprising:

a cannula sized for insertion through an opening in the normal human maxillary alveolar ridge bone towards the Schneiderian membrane, a connector and a balloon, the cannula has an external thread to be engaged with the bony walls of the alveolar ridge bone below the Schneiderian membrane, at least part of the balloon being inside the cannula, a distal part of the connector being connected to the cannula, a proximal part of the connector has a first opening so when advancing a first flowable material though the first opening, the first flowable material pass through the cannula inside the maxillary sinus to elevate the Schneiderian membrane, the proximal part of the connector has a second opening so when advancing a second flowable material though the second opening, the second flowable material being inserted inside the balloon so as to expand at least part of the balloon inside the maxillary sinus to elevate the Schneiderian membrane.

According to a further feature of the present invention, the first flowable material being advanced distally to the distal end of the cannula.

According to a further feature of the present invention, at least part of the balloon being expanded distally to the distal end of the cannula.

According to a further feature of the present invention, the first opening of the connector being connected to a first filling tube and the second opening being connected to a second filling tube.

According to a further feature of the present invention, the first filling tube being connected to a first injecting element.

According to a further feature of the present invention, the second filling tube being connected to a second injecting element.

According to a further feature of the present invention, the first injecting element has a pressure measuring device.

According to a further feature of the present invention, the second injecting element has a pressure measuring device.

According to a further feature of the present invention, the first injecting element has a piston which can be advanced by screwing.

According to a further feature of the present invention, the second injecting element has a piston which can be advanced by screwing.

According to a further feature of the present invention, the balloon has an elongated body and a wider base, the wider base being located proximally to the elongated body.

According to a further feature of the present invention, the connector being connected to the cannula by friction.

According to a further feature of the present invention, the connector being connected to the cannula by screwed connection.

According to a further feature of the present invention, the connector being connected to the cannula by a snap connection.

According to a further feature of the present invention, the connector has a clip to enable an easy detachment of the connector from the cannula.

According to a further feature of the present invention, the cannula has an internal anti-rotational element.

According to a further feature of the present invention, the cannula has an external anti-rotational element.

According to a further feature of the present invention, the device further includes a tool to be connected to the cannula from the side to enable rotating the cannula.

According to a further feature of the present invention, the connector has an external anti-rotational element and the device further includes a tool to be connected to the connector from the side to enable rotating the connector and the cannula.

According to a further feature of the present invention, the cannula has an external slot at its proximal part to enable connection to the connector.

According to a further feature of the present invention, the balloon has a wider base, the wider base has a noncircular shape.

According to a further feature of the present invention, the balloon has a wider base, the wider base has a hole to allow the passage of the first flowable material advanced through the first opening in the connector.

According to a further feature of the present invention, the balloon has a wider base, the wider base being outside the cannula.

According to a further feature of the present invention, the balloon has a wider base, the wider base being inside the cannula.

According to a further feature of the present invention, the cannula has a first internal channel and a second internal channel, the first flowable material being advanced from the first opening of the connector to pass through the first internal channel of the cannula, at least part of the balloon being inside the second internal channel of the cannula.

According to a further feature of the present invention, the distal end of the external wall of the first internal channel of the cannula being located proximally to the distal end of the internal wall of the first internal channel of the cannula.

According to a further feature of the present invention, a proximal part of the cannula has a non-circular configuration to allow connection to the connector in a predetermined relation.

According to a further feature of the present invention, the connector includes an elongated projection to be inserted inside the cannula adjacent the balloon and displaced from the internal wall of the cannula.

According to a further feature of the present invention, the distal end of the elongated projection being adjacent the distal end of the cannula.

According to a further feature of the present invention, the cannula has an opening at a side wall of the cannula adjacent the distal end of the cannula.

According to a further feature of the present invention, the connector has a distally protruding tube protruding distally inside the balloon.

According to a further feature of the present invention, the distal end of the distally protruding tube being adjacent the distal end of the cannula.

According to a further feature of the present invention, the distal end of the distally protruding tube being rounded.

According to a further feature of the present invention, the balloon being fixated to the connector.

According to a further feature of the present invention, the balloon being glued to the connector.

According to a further feature of the present invention, the balloon being fixated to the second filling tube.

According to a further feature of the present invention, the balloon being glued to the second filling tube.

According to a further feature of the present invention, a first proximally protruding tube protrudes proximally from the first opening of the connector.

According to a further feature of the present invention, a second proximally protruding tube protudes proximally from the second opening of the connector.

According to a further feature of the present invention, a first filling tube being connecting the first proximally protruding tube to a first injecting element.

According to a further feature of the present invention, a second filling tube being connecting the second proximally protruding tube to a second injecting element.

According to a further feature of the present invention, a second connector connects the second proximally protruding tube to the second filling tube, the second proximally protruding tube has internal threads, a distal part of the second connector has external threads so when the distal part of the second connector being screwed inside the second proximally protruding tube a wider base of the balloon being pressed and fixated.

According to a further feature of the present invention, a second connector connects the second proximally protruding tube to the second filling tube, the second proximally protruding tube has external threads, a distal part of the second connector has internal threads so when the distal part of the second connector being screwed over the second proximally protruding tube, a wider base of the balloon being pressed and fixated.

According to a further feature of the present invention, the second connector has a wider region to enable easy screwing.

According to a further feature of the present invention, the second connector has a proximally protruding tube to be connected to the second filling tube.

According to a further feature of the present invention, part of the connector being part of the cannula.

According to a further feature of the present invention, the connector being part of the cannula to form one-piece.

According to a further feature of the present invention, the external thread of the cannula doesn't reach the distal end of the cannula.

According to a further feature of the present invention, the external thread of the cannula reach the distal end of the cannula.

According to a further feature of the present invention, the first flowable material includes materials that promote bone growth.

According to a further feature of the present invention, the first flowable material being different from the second flowable material.

According to a further feature of the present invention, the cannula has two external threads, each external thread has a thread pitch of 1.5-2.5 mm.

According to a further feature of the present invention, the cannula has two external threads.

According to a further feature of the present invention, the cannula being tapered so its distal end being narrower than its proximal end.

According to a further feature of the present invention, the largest external diameter of the intra-bony part of the cannula is 2-4 mm.

According to a further feature of the present invention, the largest internal diameter of the intra-bony part of the cannula is 1-3 mm.

According to a further feature of the present invention, the balloon has an elongated body and a wider base, the external diameter of the elongated body is 1.0-3.0 mm, the external diameter of the wider base is 2-6 mm.

According to a further feature of the present invention, at least one of the injecting elements has a pressure measuring device.

According to a further feature of the present invention the at least part of the balloon being expanded and advanced distally to the distal end of the cannula along the central longitudinal axis of the cannula.

According to a further feature of the present invention at least one of the injecting elements has a piston which can be advanced by screwing.

According to a further feature of the present invention the first flowable material is passing between the balloon and the inner wall of the cannula while touching the inner wall.

According to a further feature of the present invention the first flowable material being laterally to the periphery of the balloon inside the cannula during the advancing of the first flowable material.

According to a further feature of the present invention the first flowable material surrounds at least the majority the balloon inside the cannula during the advancing of the first flowable material.

According to a further feature of the present invention, the balloon has an elongated body and a base, the length of the elongated body of the balloon is 2 mm-20 mm, the external diameter of the elongated body of the balloon is 1-4 mm, the base being wider than the elongated body.

According to a further feature of the present invention, the external diameter of the distal end of the cannula is 2-5.5 mm.

According to a further feature of the present invention, the external diameter of the distal end of the cannula is 2.5-4.7 mm.

According to a further feature of the present invention, the external diameter of the distal end of the cannula is 3-4 mm.

According to a further feature of the present invention, the largest external diameter of the most distal 3 mm of the cannula is 2-5.5 mm.

According to a further feature of the present invention, the largest external diameter of the most distal 3 mm of the cannula is 2.5-4.7 mm.

According to a further feature of the present invention, the largest external diameter of the most distal 3 mm of the cannula is 3-4 mm.

According to a further feature of the present invention the length of the cannula is 6-25 mm.

According to a further feature of the present invention the length of the cannula is 8-20 mm.

According to a further feature of the present invention the length of the cannula is 10-18 mm.

According to a further feature of the present invention the external thread of the cannula extends along 5-20 mm.

According to a further feature of the present invention the external thread of the cannula extends along 8-15 mm.

According to a further feature of the present invention the external thread of the cannula extends along 10-13 mm.

BRIEF DESCRIPTION OF THE DRAWINGS

The invention is herein described, by way of example only, with reference to the accompanying drawings, wherein:

FIG. 5 is a sectional view of the maxillary sinus illustrating an embodiment of passing a drill through an embodiment of the a cannula and drilling through the floor of the maxillary sinus.

FIG. 6 is a perspective view of an embodiment of a cannula in which the external thread reach the distal end of the cannula and illustrating an embodiment in which the side wall of the cannula has a hole adjacent the distal end of the cannula.

FIG. 7 is a perspective view of an embodiment of the a cannula in which the external thread doesn't reach the distal end of the cannula and illustrating an embodiment in which the side wall of the cannula has a hole adjacent the distal end of the cannula.

FIG. 8 is a sectional view of the maxillary sinus illustrating an embodiment of a device and an embodiment of a method to safely perforate the floor of the maxillary sinus in which an embodiment of a cannula being rotated while having inside a pressurized flowable material.

FIG. 13 is a sectional view of the maxillary sinus illustrating an embodiment method of advancing an embodiment of a cannula above the floor of the maxillary sinus after the Schneiderian membrane was elevated by the flowable material.

FIG. 14 is a sectional view of the maxillary sinus illustrating an embodiment method of a balloon inside an embodiment of a cannula.

FIG. 15 is a sectional view of the maxillary sinus illustrating an embodiment method of expanding a balloon inside the maxillary sinus while being surrounded by the flowable material that was previously inserted to further elevate the Schneiderian membrane.

FIG. 16 is a perspective view illustrating of an embodiment of a balloon.

FIG. 21 is a sectional view illustrating an embodiment of a balloon inside an embodiment of a cannula.

FIG. 22 is a sectional view illustrating an embodiment of a balloon connected to an embodiment of a connector having two openings.

FIG. 23 is a perspective view illustrating of an embodiment of a balloon.

FIG. 24 is a sectional view illustrating an embodiment of assembling an embodiment of a cannula, an embodiment of a balloon, an embodiment of a connector and embodiments of injecting elements.

FIG. 27 is a sectional view illustrating an embodiment of a balloon connected to an embodiment of a connector having two openings and a distally protruding element.

FIG. 28 is a sectional view illustrating an embodiment of assembling an embodiment of a cannula, an embodiment of a balloon, an embodiment of a connector and embodiments of injecting elements.

FIG. 29 is a sectional view illustrating an embodiment of assembling an embodiment of a cannula, an embodiment of a balloon, an embodiment of a connector and an embodiment of a second connector.

FIG. 30 is a sectional view illustrating an embodiment of assembling an embodiment of a cannula, an embodiment of a balloon, an embodiment of a connector and an embodiment of a second connector.

FIG. 35 is a sectional view illustrating an embodiment of a connector in which the first filling tube being connected to the side wall of the connector.

FIG. 36 is a perspective view illustrating the fixating ring used to fixate the balloon to the connector of FIG. 35.

FIG. 37 is a sectional view illustrating an embodiment of a connector in which the first filling tube and the second filling tube being connected to the side wall of the connector and the connector includes an anti-rotational element.

FIG. 38 is a sectional view illustrating an embodiment of cannula that has two proximal openings. The second proximal opening is connected to the second filling tube through a connector which is connected to the cannula by a snap connection.

DESCRIPTION OF THE PREFERRED EMBODIMENTS

Figure 1:
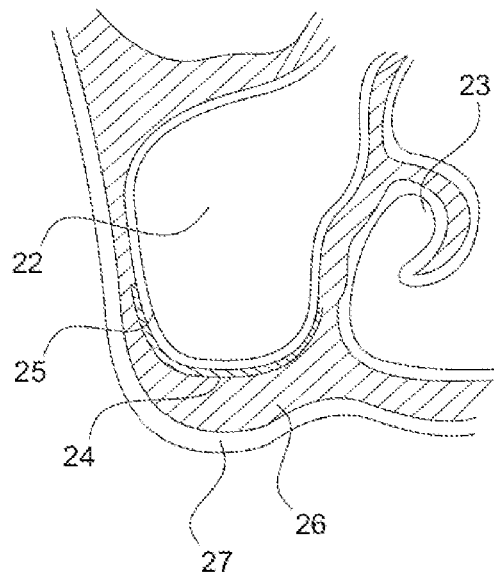
FIG. 1 is a sectional view illustrating the maxillary sinus.

Before turning to the features of the present invention in more detail, it will be useful to clarify certain terminology as will be used herein in the description and claims. It is noted that a large number of different types of materials are known which may be inserted within the body during a surgical procedure and which later dissipate, thereby avoiding the need for a separate surgical procedure for their removal. Such materials are properly referred to, depending upon the mechanism by which the material dissipates, as "bioresorbable", "bioabsorbable" or "biodegradable". Despite the differences between these different classes of materials, the aforementioned terminology is widely used interchangeably by medical professionals. Accordingly, and for conciseness of presentation, only one of these terms will generally be used in the following description, without implying the exclusion of the other classes of materials. Additionally, the phrase "bio-dissipative material" is used herein in the description and claims to refer generically to any and all materials which dissipate without requiring surgical removal, independent of which mechanisms such as dissolution, degradation, absorption and excretion take place. The actual choice of which type of materials to use may readily be made by one ordinarily skilled in the art.

The bone can be regenerated by several biological mechanisms: Osteogenesis in which the bone augmenting material includes bone forming cells; Osteoinduction in which the bone augmenting material includes materials that induce cells to form bone or to differentiate to become bone forming cells; Osteoconduction in which the bone augmenting material provides a scaffold for bone forming cells; or Osteopromotion in which encouraging the biologic or mechanical environment of bone regeneration. The bone augmenting material can be an autograft, an allograft, a xenograft, an alloplast, a cytokine, a hormone, a growth factor, a physiologically acceptable drug, a biological modifier, a protein (for example Bone Morphogenetic Protein (like BMP-2, BMP-7)), an antigen, a cell chemotaxis stimulator material, a material inducing osteogenesis, an osteoinduction material, an osteoconduction material, a bioactive material, a bioresorbable material, a bioabsorbable material, a bio-dissipative material and any combination thereof. The bone augmenting material can include materials that occupy a space in the body for at least several months. These materials preferably encourage the tissue to grow inside the space occupied by the filling material. This is the principle function of most bone augmenting materials available on the market. The bone augmenting material can be entirely bio-dissipative. The bone augmenting material can be available in the market like hydroxyapatite, bovine mineral (e.g. Bio-Oss available from Geistlich, Swiss), demineralized frizzed dried bone allograft, synthetic materials like PLA or suspension of bovine mineral in a liquid medium. The bone augmenting material can be also fully or partially not bio-dissipative, for example crystal hydroxyapatite. The bone augmenting material can include therapeutic materials.

The bone augmenting material can be a biocompatible filing material that sets and becomes rigid inside the tissue. The biocompatible filling material can be a bio-dissipative material that contains materials assisting in the process of bone healing like bone cements, for example Skeletal Repair System (SRS) from Norian company, Healos from Orquest company, OsteoGenics and Orthovita's Orthocomp from Howmedical Leibinger company.

Most bone augmenting materials are available as particles in the size of 200-2000 microns. To allow easy insertion preferably the particles are mixed with a solution like saline, blood or biocompatible gels like cellulose, glycerol and hydrogel. The bone augmenting material can be high viscous gel like Dinagraft which is gelatinous allograft bone augmenting material or with bone cements calcium sulfate or calcium carbonate.

Additionally, the phrase "augmenting material" is used herein in the description and claims to refer generically to any and all these mechanisms and in all mediums and/or gels in which these materials are mixed with. The actual choice of which type of materials to use may readily be made by one ordinarily skilled in the art.

The term "distal end" or "distal part" means the side of an element that is closer to the patient. The term "proximal end" or "proximal part" means the side of the element that is close to the dentist. "Distally" means more towards the patient and "proximally" closer to the dentist.

The term "normal human patient" means an adult human patient having conventional jaws, alveolar ridge width and mouth sizes. This means that the claimed devices of the present applications are sized to be inserted to mouths and through the alveolar ridges of the vast majority of adult human patients. If a device can be inserted only inside the mouth of giants or through extraordinary wide alveolar ridges, it is not part of this patent application. For example, devices, like the devices which are used for orthopedic surgery or abdominal surgery, are usually too big to be inserted inside the mouth or through the normal human alveolar ridge and are not part of this application. The present application describes a cannula which is inserted through the alveolar ridge bone. If the diameter of the inserted part of the cannula is more than 6 mm it is too wide for many human patients and not part of this patent application.

The description mentions several times "protruding" and/or "projecting" element and/or tubes. These elements and and/or tubes can be also internal elements or sockets, which don't protrude, if it is practically feasible. For example, although a protruding tube is mentioned to protrude distally or proximally from a component and being connected to another conduit, it is also possible that the tube is inside the component and the conduit is connected by insertion inside the tube instead of the tube to protrude from the component.

Finally with respect to terminology, reference will be made to a flowable material used to fill the space below the Schneiderian membrane and/or inside the balloon of the present invention. It should be noted that this flowable material may assume a wide range of compositions and consistencies, so long as the filling material may be inserted into the sinus and/or the balloon. Thus, possible consistencies for the filling material include, but are not limited to, consistencies described as watery, viscous, gelatinous, moldable, waxen, particulate, and suspensions or mixtures combining any of the above. The filling material can be liquid like saline.

The filling material can be also any kind of a bone augmenting material described above.

Turning now in detail to the drawings, which depict the presently preferred embodiments of the invention for the purpose of illustrating the practice thereof and not by way of limitation of the scope of the invention, and in which like reference characters refer to corresponding elements throughout the several views.

FIG. 1, illustrates the maxillary sinus 22, the nasal cavity 23 the floor of the maxillary sinus 24, the Schneiderian membrane 25 covering the floor of the maxillary sinus 24, the maxillary alveolar ridge bone 26 below the maxillary sinus 22 and the gums 27 covering the maxillary alveolar ridge bone 26. The height of the maxillary alveolar ridge bone 26 in FIG. 1 is less than 10 mm.

Figure 2:
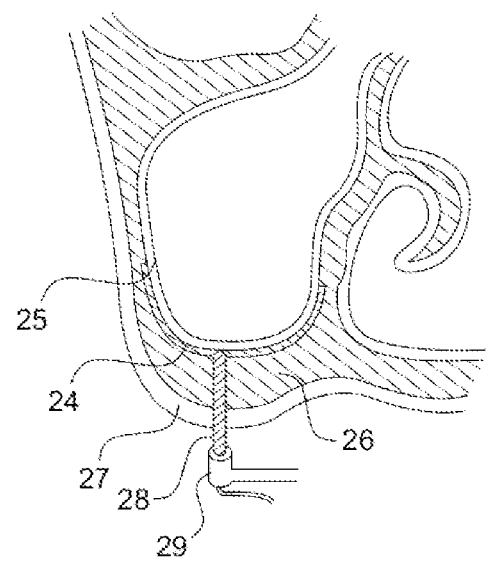
FIG. 2 is a sectional view of the maxillary sinus illustrating drilling through the alveolar ridge bone.

Embodiments of novel methods for using embodiments of novel devices are illustrated in the following views. The purpose of the following embodiments is to displace the Schneiderian membrane 25 from the floor of the maxillary sinus 24 to create a space above the floor of the maxillary sinus 24 and beneath the Schneiderian membrane 25. The first step can be to creating a path of insertion through the maxillary alveolar ridge bone 26 from the oral cavity towards the Schneiderian membrane 25. This path of insertion can be created by drilling using a physio-dispenser through the maxillary alveolar ridge bone 26 and optionally also through the gums 27 until touching the floor of the maxillary sinus 24 as illustrated in FIG. 2. Several drills in ascending diameters can be used as is the technique in the osteotomy for dental implants. It is also possible to raise a mucoperiosteal flap before the drilling. It is also possible to create the path of insertion using other types of drills for example a high-speed round drill or/and low speed drill 28 inside a handpiece 29. It is also possible to do the osteotomy with osteotomes instead of drilling.

Figure 3:
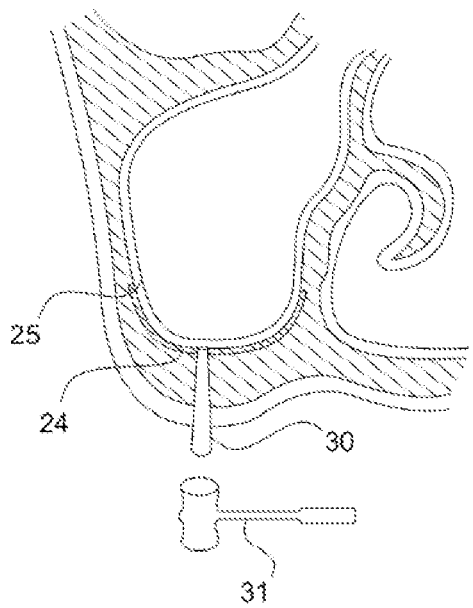
FIG. 3 is a sectional view of the maxillary sinus illustrating the use of an osteotome.

After the floor of the sinus is reached it is possible to insert an osteotom 30 through the osteotomy and using a mallet 31 to gently break the floor of the maxillary sinus 24 crating a green stick fracture as illustrated in FIG. 3. Perforating the floor of the maxillary sinus 24 can be also done by using gently and carefully drills without perforating the Schneiderian membrane 25.

Figure 4:
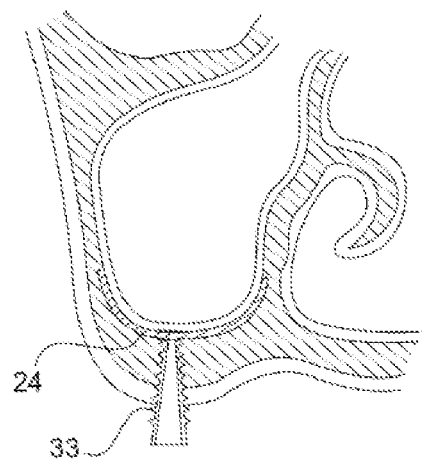
FIG. 4 is a sectional view illustrating an embodiment of a cannula inside the alveolar ridge bone adjacent the floor of the maxillary sinus.

A novel embodiment is illustrated in FIGS. 4 and 5. In this embodiment a cannula 33 can be inserted through the path of insertion so its distal end being adjacent the floor the maxillary sinus 24 and then to insert through the cannula 33 a drill 34 so it will protrude 0.25-2 mm distally outside the cannula 33 towards the Schneiderian membrane 25. The drill 34 can have a stopper to limit its protrusion outside the cannula 33. Preferably the stopper will allow protrusion of the drill 34 distally to the distal end of the cannula of about 0.5-1.5 mm or 0.75-1.25 mm.

The stopper of the drill can be in contact with the cannula. The stopper can be part of the drill or connected to drill. The stopper can be connected to the handpiece 29 holding the drill 34 and in this case it is not rotated while the drill 34 is rotating and requires adjustment to each handpiece. It is also possible that the proximal part of the cannula functions as a stopper when being in contact with the handpiece 29 as illustrated in FIG. 5. The cannula 33 can include a protrusion or several protrusions to be in contact with the handpiece 29 and function as stopper. In these configurations the stopper function with most handpieces in the market and the stopper is not rotated while the drill is rotated and there is not friction between the stopper and the cannula.

The cannula 33 can fit the diameter of the path of insertion so the alveolar ridge bone 26 will stabilize the cannula 33. The cannula 33 can be wider than the diameter of the path of insertion to enhance the stabilization of the cannula 33. To further enhance the stabilization of the cannula the cannula 33 can be tapered so the distal end 36 of the cannula 33 is narrower than the cannula 33 proximally to the distal end 36 as illustrated in FIG. 6. A further enhancement of the stabilization that will allow better control on the insertion of the cannula is that the cannula 33 will have an external thread 37 so the cannula 33 will be inserted by screwing inside the path of insertion. The external thread 37 of the cannula 33 can be sharp to preserve the bone. The cannula can have a second external thread 38 to enhance the stability of the cannula 33. The external threads 37, 38 of the cannula 33 can be also with high thread pitch, for example of 1-3 mm or 1.5-2.5 mm which can result with elastic expansion of the bone around the cannula 33. The advantage of this elastic expansion is that after the removal of cannula 33 and insertion of a dental implant, the bone will elastically relapse and compress the dental implant to better stabilize the dental implant. The thread's pitch can be also 0.5-1.5 mm or any other thread pitch. The external threads 37, 38 can reach the distal end 36 of the cannula 33 as illustrated in FIG. 6 or to end about 1-3 mm proximally to the distal end 36 of the cannula 33 as illustrated in FIG. 7. The external diameter of the cannula can be 2.0-4.0 mm or 2.5-3.5 mm, the internal diameter can be 0.7-3.5 mm or 1.0-3.0 mm or 1.5-2.5 mm. The distal part of the cannula which is the intra-bony part (intended to be inserted inside the alveolar ridge bone) can have at least one external thread along its entire length or along part of the intra-bony part. The length of the intra-bony part can be 4-20 mm or 8-16 mm or 9-13 mm. Proximally to the intra-bony part the cannula 33 can have an external anti-rotational element 44. The length of the external anti-rotational element 44 can be 1-10 mm or 3-8 mm or 4-6 mm. The external anti-rotational element can be wider than the external thread along the intra-bony part or to narrower or to have the same width. Distally to the external anti-rotational element the cannula 33 can have a lateral projection and/or several lateral projections and/or a projecting ring to serve as a distal stop to the rotating element 45 and/or the ratchet. This lateral projection can be located between the intra-bony part of the cannula 33 and the external anti-rotational element 44. The cannula 33 can have proximally to the external anti-rotational element 44 a connecting part of the cannula 33 to be connected to the connector 47. The length of the connecting part of the cannula can be 1-10 mm or 3-8 mm or 4-6 mm. The connecting part of the cannula can have an internal anti-rotational element. The internal anti-rotational element can be a polygon, for example, like a trapeze and the connector 47 can have an external distal projection in the shape of a compatible trapeze to enable a connection in only one relation between the cannula 33 and the connector 47. The connector can have an external anti-rotational element so when rotating the connector 47 the cannula 33 is also rotated.

The distal end of 36 the cannula 33 can be sharp to allow for easy insertion or to be rounded to prevent perforating the Schneiderian membrane 25 with the distal end 36 of the cannula 33. The distal end 36 of the cannula can have also small projections like a trephine drill to enhance the cutting and penetration of the cannula as illustrated in FIG. 7. The most distal part of the threads can be smaller in perpendicular to the long axis of the cannula 33 compared to a more proximally threads to reduce the risk of tearing the Schneiderian membrane 25. The cannula 33 can have an internal anti-rotational element and/or an external anti-rotational element at is proximal part. This anti-rotational element can be used with an insertion tool for inserting the cannula 33 inside the alveolar ridge bone 26. The anti-rotational element can be for example a polygon like a hexagon. The cannula 33 can have lines and/or colors indicating the depth of insertion of the cannula 33 inside the alveolar ridge bone 26. The cannula 33 can have a side perforation 39 adjacent the distal end 36 of the cannula 33 or even several side perforations adjacent the distal end 36 of the cannula 33.

The drill 34 can have flat distal end and the distal end of the drill 34 can be coated with diamond powder and/or to have blades at the distal end of the drill. The diamond powder and/or the blades can be only at the flat surface of the drill facing the Schneiderian membrane. The distal end of the drill can be rounded or just rounded at the borders. The distal end of the drill can be also concave so bone particles will be aggregated and reduce the chance for tearing the Schneiderian membrane 25. The side walls of the drill can be smooth and/or narrower than the distal end of the drill 34 to prevent contact and grinding of the cannula 33. The drill 34 can be active only on its distal end facing the sinus.

If after advancing and using the drill 34 inside the cannula 33, the floor of the maxillary sinus 24 is still not perforated, the cannula 33 can be slightly advanced towards the Schneiderian membrane 25 and the drill 34 inside the cannula 33 activated again until perforating the floor of the maxillary sinus 24. This step can be done several times advancing gradually the cannula 33 and activating the drill 34 until perforating the floor of the Maxillary sinus 24.

After perforating the floor of the maxillary sinus 24 without perforating the Schneiderian membrane 25, a distal end of flexible tube 41 can be connected to the cannula 33 and the proximal end of the tube 41 can be connected to an injecting element like a syringe 42 or a pump as illustrated in FIG. 8. The injecting element 42 can have a pressure measuring element 43. The injecting element can be also for example the pump of devices which common in dental clinics for example a physio-dispenser device or a Wand injecting device (available from Wand dental Inc.) which can be activated continuously and therefore create continuous pressure. Increasing the power of the pump of these devices can increase the pressure inside the cannula (and/or the osteotome as described hereafter).

The tube 41 can be connected to the injecting element 42 and/or the cannula 33 by a screwed connection like a Luer connector or by friction connection or any other watertight connection. The tube 41 can have a connector 47 at its distal end and/or at its proximal end. This connector/s can have internal threads and/or external threads whereas the injecting element and/or the cannula can have compatible external thread and/or internal thread.

Figure 9:
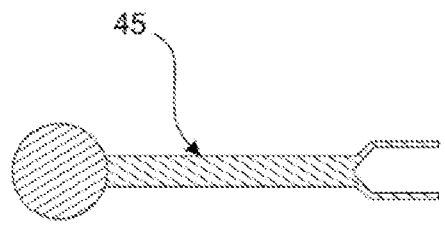
FIG. 9 is a perspective view of an embodiment of a stabilizing tool that can be also used to rotate the cannula. The stabilizing tool can be connected to the cannula from the side.

If the connection of the tube 41 to the cannula 33 is by a screwed connection the cannula 33 can have an external anti-rotational element 44 that can be hold by a stabilizing tool 45 as illustrated in FIG. 9 so the cannula 33 will not rotate while connecting the tube 41 to the cannula 33. The anti-rotational element 44 can be for example an external hexagon and the stabilizing tool 45 coming from the side and engaging at least two planes of the external hexagon.

Figure 10:
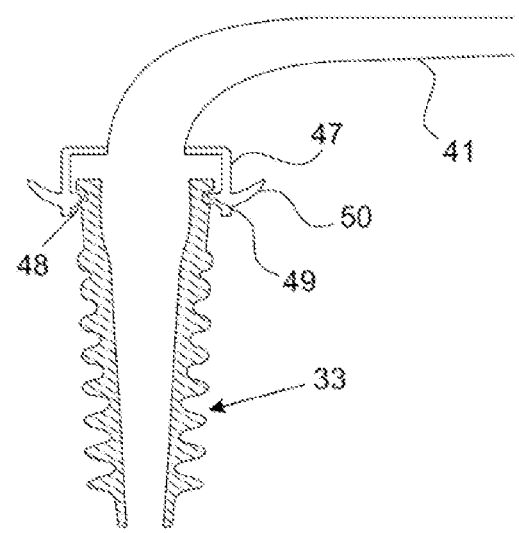
FIG. 10 is a sectional view illustrating an embodiment of connecting an embodiment of a connector with an embodiment of a cannula without rotating the connector.

The connection of the tube 41 to the cannula 33 can be by friction. For example the distal end of the tube 41 can be placed over the proximal end of the cannula 33. The proximal region of the cannula 33 can have a narrower region distally to the proximal end, for example a slot 48 as illustrated in FIGS. 6, 7. The distal end of the tube 41 can have a flexible connector 47 having a narrower region 49 as illustrated in FIG. 10. After sliding the connector 47 over the proximal region of the cannula 33 the narrower region 49 of the connector 47 engages the slot 48 of the cannula 33. This configuration strengthens the connection and prevents the detachment of the tube under high pressure. The proximal region of the cannula can be tapered proximally to enable easy sliding of the connector 47 over the proximal region of the cannula 33. The connection between the connector 47 and the cannula 33 can be a snap connection.

The connector 47 can include a clip 50 to strengthen the connection and prevent the detachment of the tube 41 under high pressure. The clip 50 can be used together with a narrower region 49 in the connector 47. The clip 50 can have protrusions that will be accessible to dentist to allow for easy detachment of the tube 41 without pulling strongly the cannula 33 because the cannula 33 can be fixated by small and soft bone.

A connector like the described above or any other connection without a thread reduce the risk of rotating the cannula 33 during the connection and/or detachment of the tube 41 and therefore don't compromise the stability of the cannula 33 along the procedure.

After connecting the tube 41 to the cannula 33 and to the injecting element 42, the injecting element 42 can be activated. The injecting element 42 can have a flowable material which is liquid, for example, saline or a material that includes saline. The flowable material can be also a flowable material with a radiopaque material to be visible in X-Ray. Preferably the flowable material is a biocompatible material. If the pressure measuring device 43 shows a high pressure (500-1000 mmHg above room pressure) this can indicate that the floor of the maxillary sinus 24 is not perforated. In this case the cannula 33 can be advanced about 1 mm and then activating the injecting element 42 again. It is also possible to disconnect the tube 41 and drill thought the cannula 33 and then to connect again the tube 41.

Figure 11:
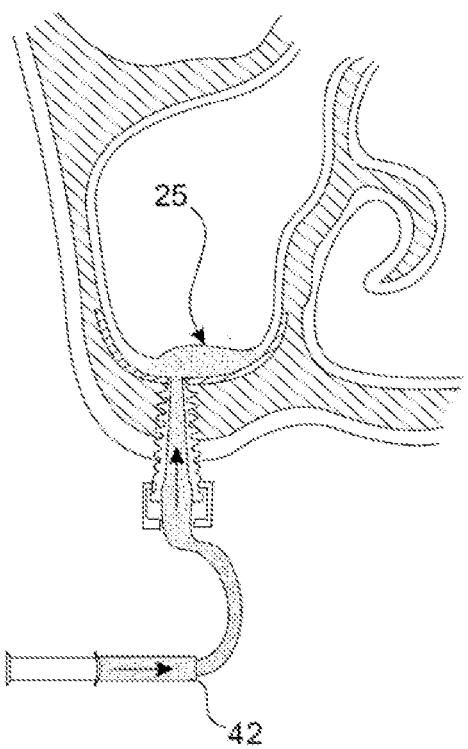
FIG. 11 is a sectional view of the maxillary sinus illustrating the Schneiderian membrane being elevated by a pressurized flowable material.

If there is a perforation in the Schneiderian membrane 25, the saline will be advanced without almost no increase in the pressure. If the floor of the maxillary sinus 24 is perforated and the Schneiderian membrane 25 remains intact there will be an increase in the pressure while inserting the flowable material and almost no pressure when no more flowable material is inserted. This behavior can indicate that the Schneiderian membrane 25 is intact and elevated as illustrated in FIG. 11.

Figure 12:
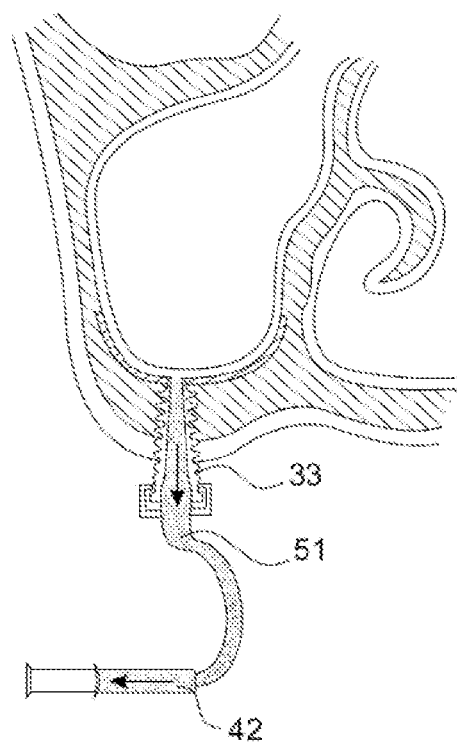
FIG. 12 is a sectional view of the maxillary sinus illustrating a method of validating the integrity of the elevated Schneiderian membrane in which the Schneiderian membrane being moved back towards the floor of the maxillary sinus by extracting the flowable material from the sinus.

The integrity of the Schneiderian membrane 25 can be also validated without the use of a pressure measuring element 43. The simplest way is to extract back the flowable material from the maxillary sinus with the injecting element 42. If the Schneiderian membrane 25 is not perforated the flowable material will return to the tube 41 with some blood 51 as illustrated in FIG. 12. If the measuring element 43 is used while extracting the flowable material the pressure can be negative.

It is better to fill the tube 41 with the flowable material before connecting it to the cannula 33 so there will be almost no air in the tube 41.

The amount of flowable material to be injected is dependent on the amount of elevation of the Schneiderian membrane 25 that is required. In most of the cases the amount is 0.5-2 ml and usually 0.7-1.3 ml.

The device illustrated in FIG. 8 can be also used differently to achieve a safe perforation of the floor of the maxillary sinus 24 without perforating the Schneiderian membrane 25. In this method the cannula 33 is inserted so the distal end 36 of the cannula 33 will be about 1 mm below the floor of the maxillary sinus 24 as illustrated in FIG. 4 and then the proximal end of the tube 41 can be connected to the injecting element 42 and the distal end of the tube 41 can be connected to the cannula 33 by the connector 47 as illustrated in FIG. 8. The tube 41 and/or the cannula 33 can be filled with the filling material before connecting the tube 41 to the cannula 33 to reduce the amount of air in the device. After connecting the tube 41, the injecting element 42 can be activated so as to increase the pressure in cannula 33. If the injecting element 42 is a simple syringe with a piston, the piston can move unintentionally backwards as a result of this pressure so the pressure will be reduced. To avoid unintentional movement, the piston can have for example a thread and to be advanced by rotating. The piston can have also small protrusion and a locking mechanism preventing back movements. The injecting element 42 can be a pump that controls the pressure. The injecting element 42 and/or the tube 41 can have a pressure measuring device. After there is a pressure in the tube 41 which is higher than the room pressure (for example 100-700 mmHg above room pressure) the cannula 33 can be rotated and advanced until breaking the floor of the maxillary sinus 24. The cannula 33 can be rotated by the stabilizing element 45 illustrated in FIG. 9 coming from the side. The anti-rotational element of the cannula can be any polygon for example triangular, square, hexagon or octagon. If the anti-rotational element has more surfaces it will be easier to use a compatible stabilizing element 44 between adjacent teeth since the stabilizing element can be inserted in more angles between the teeth without touching the teeth. The anti-rotational element of the cannula can also include protrusions and/or sockets and/or any other morphology that enables rotating the cannula. It can be also rotated by a ratchet that can slide over the tube 41 or to be connected to the cannula 33 before connecting the tube 41 to the cannula 33. The stabilizing element 45 or the ratchet can engage the anti-rotational element 44 of the cannula 33. The stabilizing element 45 or the ratchet can engage an anti-rotational element of the connector 47. The cannula 33 can be also advanced by other means. When the floor of the maxillary sinus 24 is perforated the pressurized filling material, for example the saline, can penetrate through the perforation in the floor of the maxillary sinus 24 under the pressure and elevate the Schneiderian membrane 25. When the Schneiderian membrane 25 being elevated, the pressure indicated in the pressure measuring device 43 will be reduced indicating the perforation of the floor of the maxillary sinus. After this reduction in the pressure, the injecting element 42 can be activated to insert more flowable material to the maxillary sinus. The amount of flowable material to be injected is dependent on the amount of elevation of the Schneiderian membrane 25 that is required. In most of the cases the amount is 0.5-2 ml and usually 0.7-1.3 ml. Then the integrity of the Schneiderian membrane can be validated as described above, for example, by activating the injecting element 42 to extract the filling material from the maxillary sinus 24.

This method of using the device of FIG. 8 by rotating the cannula 33 while having pressure inside the cannula 33 enables a safe perforation of the floor of the maxillary sinus 24 and elevation of the Schneiderian membrane 25 without creating a tear in the Schneiderian membrane 25. This is because when there is a small perforation in the floor of the maxillary sinus 24 the flowable material immediately pass from the cannula 33 through the floor of the maxillary sinus 24 and elevate the Schneiderian membrane 25. This immediate elevation protects the Schneiderian membrane 25 from being perforated by the advancing cannula 33. This method is safer than the method of using the drill with the cannula as a stopper described above because in this method there is no drill which is rotating fast and can be in direct contact with the Schneiderian membrane 25. When using a conventional drill with internal irrigation there is also some pressure inside the osteotomy that can elevate the Schneiderian membrane 25. But since the drill is rotated in high speed and the pressure is low, it is depend on the control of the dentist on the drill so the risk of perforating the Schneiderian membrane 25 is higher. The pressure when drilling with a drill with internal irrigation is low because the flowable material can leak through the osteotomy, it is not a closed system. In the above described method, the system is closed and the flowable material can't leak through the osteotomy because the osteotomy is closed by the cannula 33. In the described above method the hand control of the dentist is not so important as when drilling. The dentist is just rotating slowly the cannula 33. It is recommended to rotate very slowly the cannula 33 and to look all the time on the pressure measuring element 43 so as to stop immediately rotating the cannula 33 when the pressure drops.

A different method of safe perforation of the floor of the maxillary sinus while preserving the integrity of the Schneiderian membrane can be done using a novel osteotome instead of a drill or a cannula having an external thread. Some principles of the osteotome's method and device are similar to the cannula's method and device, however the osteotome's method and device are different. The osteotome doesn't require an external thread as the cannula. To avoid repeating the same description, the osteotome's method and device will be described hereafter shortly while the cannula's method and device will be described in more detail with more embodiments and examples. Nevertheless most of the Cannula's embodiments can be used also in the osteotome's method and device, although these are different methods and devices. For example, many combinations of a cannula and balloon are described and accordingly many combinations of an osteotome and a balloon can be used, while these combinations are almost not described hereafter.

Figure 45:
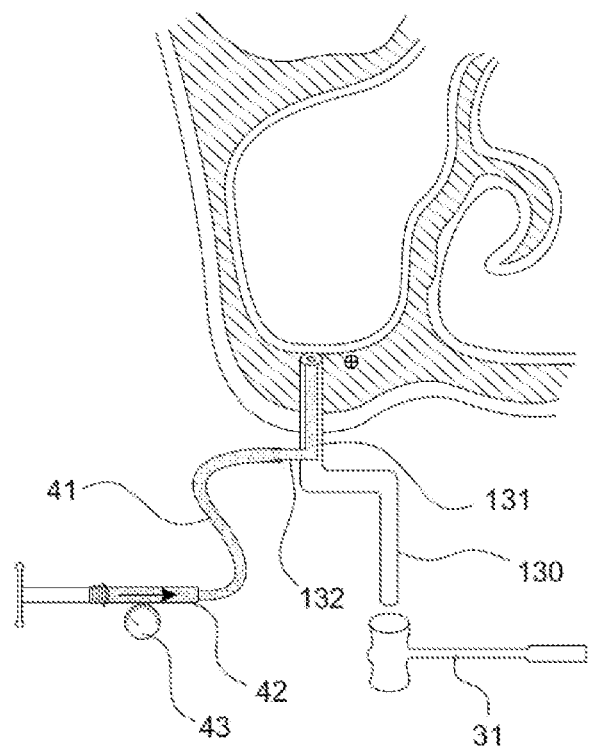
FIG. 45 is a sectional view of the maxillary sinus illustrating an embodiment of a device and an embodiment of a method to safely break the floor of the maxillary sinus by using a novel osteotome which is hammered inside the alveolar ridge while having inside a pressurized flowable material.
Figure 46:
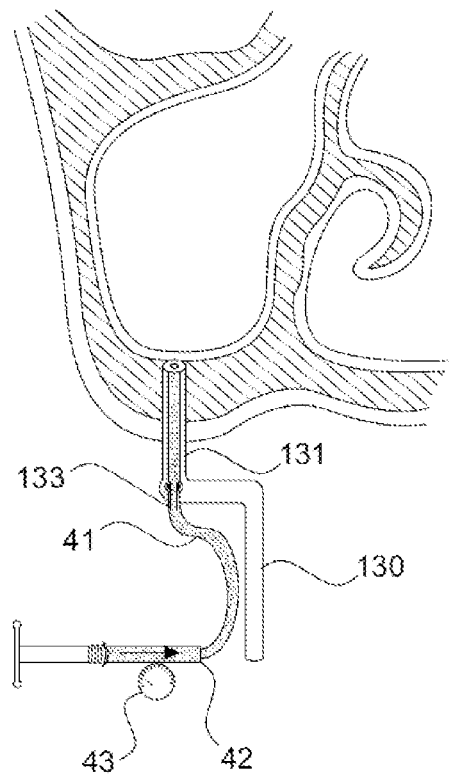
FIG. 46 is a sectional view of the maxillary sinus illustrating an embodiment of a device and an embodiment of a method to safely break the floor of the maxillary sinus by using an osteotome which is hammered inside the alveolar ridge while having inside a pressurized flowable material.

FIG. 45 illustrates an osteotome 130 that can be straight or bended. The distal part 131 of the osteotome 130 has an internal channel extending from a distal opening at the distal end of the osteotome to a proximal opening located along the osteotone 130. The proximal opening can be for example at a side wall of the distal part 131 of the osteotome. If the osteotome 130 is bended the proximal opening can be at the bending point as illustrated in FIG. 46 so the internal channel is straight and not bended. It is recommended that the internal channel will not be too narrow to prevent it from being blocked by bone particles and to allow cleaning of the internal channel. For example, the external diameter of distal edge of the osteotome 130 can be 2-4 mm and diameter of the internal channel 1-2 mm. The distal part of the osteotome can be tapered to become narrower distally and/or to have several steps becoming narrower distally. The internal channel of the osteotome 130 can be connected to a filling tube 41 that can be connected to an injecting element 42 having a filling material. The injecting element 42 can have pressure measuring device 43. The filling tube can be connected to the osteotome 130 in various ways, for example, the ostetome can have a tube 132 protruding from the proximal opening as illustrated in FIG. 45. The filling tube 41 can be connected to the osteotome through a detachable connector 133 which can be a screwed connector and/or a snap connector and/or any other known connector of tubes.

The injecting element 42 can be activated to increase the pressure inside the injecting element and then the osteotome can be activated by a mallet 31 until fracturing the floor of the sinus. After a fracture is created the pressurized filling material will enter the sinus through the fracture and elevate the Schneiderian membrane as explained above for FIG. 8. The mallet 31 can be also a mechanical mallet and/or a magnetic mallet, for example the magnetic mallet available from Meta Ergonomics, Italy.

The initial insertion of the cannula and/or the osteotome can be done while a temporary closing pin being inside the internal channel of the cannula and/or osteotome to prevent bone particles from entering inside the internal channel. The temporary closing pin can be removed before activating at least one of the injecting elements.

After the injection of the flowable material and extracting the flowable material to validate that the Schneiderian membrane is not perforated the flowable material can be reinserted to the sinus so about 1 ml is inside the sinus. Then the tube 41 can be disconnected from the cannula 33 or the osteotome 130. The cannula 33 (or the osteotome) can be advanced deeper so its distal end will be above the floor of the maxillary sinus 24 as illustrated in FIG. 13.

A balloon 55 can be inserted inside the cannula 33 (or the osteotome 130) as illustrated in FIG. 14. After the insertion of the balloon 55, the tube 41 can be connected again to the cannula 33. The balloon 55 can be filled with a flowable material before being inserted inside the cannula 33 or before connecting the tube 41 again. After connecting the tube 41 to the cannula 33 the injecting element 42 can be activated again and this time the flowable material is inserted inside the balloon 55 so as to expand the distal portion of the balloon 55 distally to the distal end of the cannula as illustrated in FIG. 15. The balloon 55 inside the maxillary sinus being surrounded with the flowable material 60 that was previously inserted into the sinus so expanding the balloon 55 is pushing the surrounding flowable material 60 which is pushing and further elevating the Schneiderian membrane 25. It is possible that the balloon 55 is touching part of the Schneiderian membrane 25 during the expansion so the direction and the amount of the elevation of the Schneiderian membrane 25 is dictated also by the balloon 55 and not only by the flowable material 60 inside the sinus. If the balloon 55 is not touching the Schneiderian membrane 25 then the pressure is evenly distributed according to Pascal's rule. If the balloon 55 is touching the Schneiderian membrane 25, then the pressure on the Schneiderian membrane 25 which is touching the balloon 55 is higher than the pressure on the Schneiderian membrane 25 which is not in direct contact with balloon 55, but this difference is significantly smaller compared to a situation when there is only a balloon 55 which is not surrounded by the flowable material 60 inside the sinus. Because the difference in the pressure is smaller, the tearing forces on the Schneiderian membrane 25 are smaller resulting in lower risk for tearing the Schneiderian membrane 25 while controlling the direction, amount and location of the elevation of the Schneiderian membrane 25.

Figure 17:
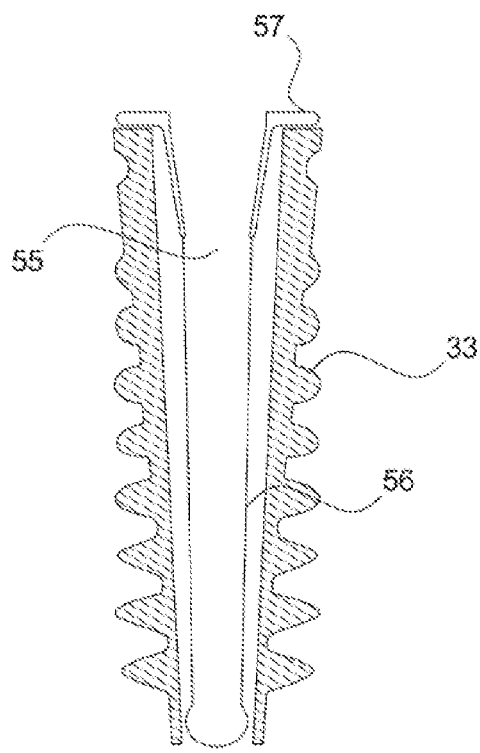
FIG. 17 is a sectional view illustrating an embodiment of a balloon inside an embodiment of a cannula.
Figure 18:
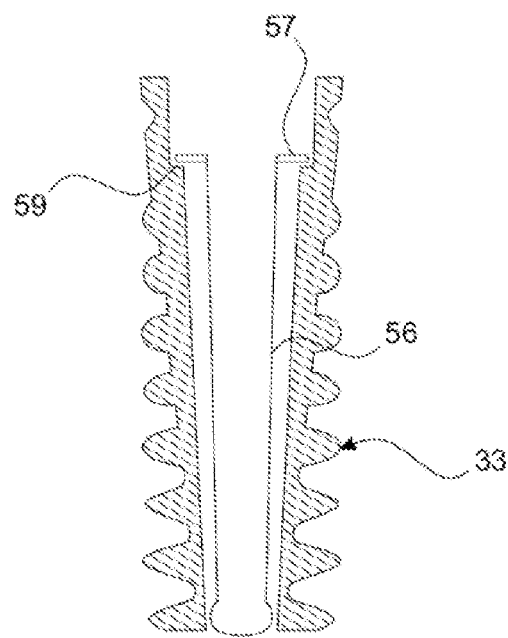
FIG. 18 is a sectional view illustrating an embodiment of a balloon inside an embodiment of a cannula.
Figure 19:
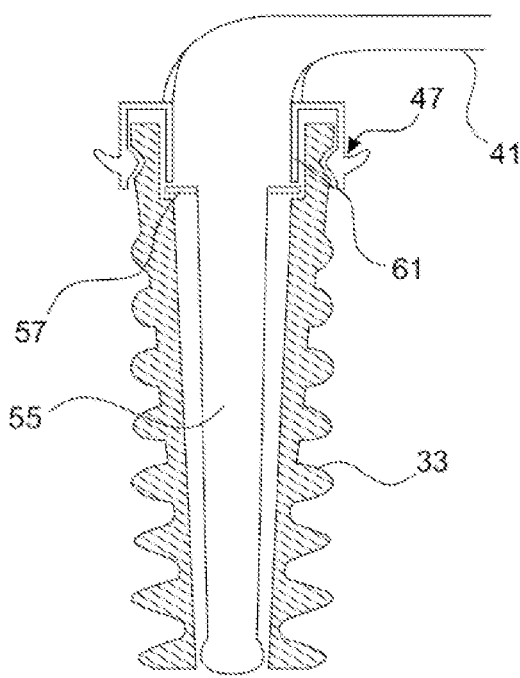
FIG. 19 is a sectional view illustrating an embodiment of connecting an embodiment of a connector with an embodiment of a cannula without rotating the connector after the insertion of an embodiment of a balloon inside the cannula.

There are several optional shapes for the balloon 55. The balloon 55 and/or the cannula 33 can be configured to ensure that the proximal portion of the balloon 55 will not pass through the cannula 33 and enter inside the maxillary sinus. The balloon 55 can have an elongated body 56 with a wider base or/and a flange or/and a shoulder 57 as illustrated in FIG. 16. The length of the body can be 5-20 mm or 8-15 mm. The external diameter of the body 56 of the balloon can be 0.5-4.5 or 0.8-4.0 mm or 1.0-3.0 mm or 1.5-2.8 mm. The base 57 of balloon can be wider than the body 56, it can have a diameter of 2-6 mm or 3-5 mm. The elongated body 56 is for insertion inside the cannula 33 and the wider base 57 is to prevent advancement of the entire balloon 55 inside the sinus while being expanded. The base 57 of the balloon 55 can engage the proximal end of the cannula as illustrated in FIG. 17. The connector 47 illustrated in FIG. 10 can press the base 57 of the balloon 55 to ensure that the flowable material which is injected will enter the balloon 55 and expand the balloon 55 and not pass between the balloon 55 and the cannula 33 inside the sinus. The base 57 of the balloon 55 can be inserted inside the cannula 33 as illustrated in FIG. 18. The cannula 33 can have a narrow region 59 to be in contact with the base 57 to prevent advancement of the base 57 inside the sinus. In this configuration the connector 47 can have a distally protruding tube 61 to protrude inside the cannula 33 and press the base 57 of the balloon 55 as illustrated in FIG. 19. The balloon 55 can be also placed over the distally protruding tube 61 so the distally protruding tube 61 will be inside the balloon 55. The balloon 55 can be fixated for example by glued to the connector 47 and/or to the distally protruding tube 61 and/or to the filling tube 41.

Figure 20:
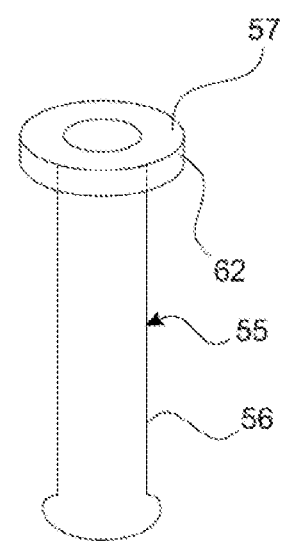
FIG. 20 is a perspective view illustrating of an embodiment of a balloon.

The base 57 can have a distal extension 62 as illustrated in FIG. 20 which will cover the external wall of the proximal part of the cannula 33 as illustrated in FIG. 21. These are some examples of the connection of the balloon 55 and the cannula 33, other options of relation, connection and fixation can be used.

After the insertion of the balloon 55 the tube 41 can be connected to the cannula 33 in the same way it was connected while inserting the flowable material inside the sinus. The flowable material for expanding the balloon 55 can be the same flowable material previously used for filling the sinus and elevating the Schneiderian membrane 25 and can be also a different filling material. For example, the filling 60 to be inside sinus can be saline and the filling material inside the balloon can include barium and be visible in X-Ray. The filling material inside the sinus can be more gelatinous and the filling material inside the balloon can be more watery. The filling material inside the balloon can be a flowable material which is liquid, for example, saline or a material that includes saline The filling material inside the sinus can be a bone augmenting material.

Although it is possible to inflate the balloon and the surrounding of the balloon with gas, this is not recommended. Inflating the surrounding of the balloon with pressurized gas can cause some gas bubbles to enter blood vessels or the tissue and cause emphysema and/or emboli. In addition, gas can be compressed so when inserting gas inside the balloon can be filled without being expanded and then to expand rapidly. When filling with liquid the expansion is better controlled. Because of this reason, if the sinus is first being filled with gas and then the balloon being expanded while being surrounded with gas the effect of the synergetic combination of the two fillings according to Pascal's law almost will not function, since the gas will be compressed and will not transfer the forces properly to elevate the membrane. Therefore, in the present application the filling material surrounding the balloon can't be entirely gas. It is also recommended that the filling material inside the balloon will have the minimum amount of gas. It is also possible to evacuate the air from the balloon before filling it. This can be done for example by using a connector to fill the balloon with two openings, so through one opening the air is taken out to form a vacuum and afterwards the filling material is inserted through the second opening of the connector to inflated the balloon.

It is recommended to inflate the balloon slowly. The amount of flowable material to be injected inside the balloon 55 is dependent on the amount of elevation of the Schneiderian membrane 25 that is required. In most of the cases the amount is 0.5-2 ml and usually 0.7-1.3 ml.

After the inflation of the balloon 55, the balloon 55 can be deflated, then the tube 41 can be disconnected from the cannula 33 and the balloon 55 taken out from the cannula 33. If the balloon 55 is completely inside the cannula 33 the balloon 55 can have a proximal protrusion to allow easy holding and withdrawn from the cannula 33. After taking the balloon 55 out from the cannula 33 the tube 41 can be connected again to the cannula 33 for extraction, with the injecting element 42, of the flowable material which was inserted before the insertion of the balloon 55. This procedure of extracting the flowable material from the sinus helps in validating the integrity of the Schneiderian membrane 55 after the expansion of the balloon 55. If the Schneiderian membrane 25 is not perforated the flowable material will return to the tube with some blood and almost without air. If the Schneiderian membrane 25 is perforated significant amount of air is going to enter the tube. The integrity of the Schneiderian membrane 25 can be also validated with the pressure measuring element 43 during extraction and/or insertion of the flowable material.

The integrity of the Schneiderian membrane can be also validated by looking directly or through an endoscope inside the sinus while the patient is breathing.

In another embodiment a different connector can be connected to the cannula 33. An embodiment of this connector is illustrated in FIG. 22. The connector 70 can have a first and second openings from which a first proximally tube 73 and a second proximally tube 74 extends proximally from the connector 70. The two proximally tubes 73, 74 being connected to two filling tubes 71, 72. The connector 70 can have a distally protruding tube 75 protruding distally which is continuous with the second proximally protruding tube 74. The balloon 55 can be placed over the second distally protruding tube that is protrudes distally 75. The second distally protruding tube protruding distally 75 can extend to adjacent the distal end of the balloon 55 to prevent folding of the balloon 55 during insertion inside the cannula 33 and during extracting the flowable material from the maxillary sinus. The distal end of the second distally protruding tube 75 can be rounded to prevent perforating the balloon 55. The base 57 of the balloon 55 can be shorter towards the second opening so not to close the second opening as illustrated in FIGS. 22, 23. The base 57 of the balloon 55 can be also perforated where it is facing the first opening of the connector 70. FIG. 24 illustrates the connection of the connector 70 and the balloon 55 to the cannula 33. The first tube 71 can be connected to a first injecting elements 42A and a second filling tube 72 can be connected to a second injecting element 42B. The first filling tube 71 is directing the flowable material from the first injecting element 42A inside the cannula 33 but outside the balloon 55. The second filling tube 72 is directing the flowable material from the second injecting element 42B inside the balloon 55. After the insertion of the cannula 33 with the balloon 55 inside the path of insertion in the alveolar ridge bone 26 adjacent the floor of the maxillary sinus 24, the first injecting element 42A is activated to create pressure. The first injecting element 42A can include a pressure measuring device 43. After creating pressure inside the first tube 71 the cannula 33 can be rotated with the stabilizing tool 45 or with a ratchet or with other tools until the distal end 36 of the cannula 33 will perforate the floor of the maxillary sinus 24 and the pressure drops after the Schneiderian membrane 25 is elevated. This is similar to the method described above but this time, the balloon 55, the connector 70 and the tubes 71, 72 are also rotated. In this embodiment there is no need to disconnect the connector before inserting the balloon and therefore the procedure is faster. When activating only the first injecting element 42A the flowable material is passing through the cannula 33 outside the balloon and inside the maxillary sinus. After the perforation of the floor of the maxillary sinus 24 more flowable material can be inserted inside the maxillary sinus by activating the first injecting element 42A and the cannula 33 can be rotated so its distal end 36 will be about 1 mm above the floor of the maxillary sinus 24. Then the second injecting element 42B can be activated so as to expand the balloon 55 inside the maxillary sinus while the balloon 55 being surrounded by the flowable material 60 that was previously inserted inside the maxillary sinus. Activating the first injecting element 42A while the balloon 55 being expanded will result in an increase of the pressure in the first filling tube 71 since the cannula 33 being blocked by the expanded balloon 55. This increase of the pressure in the first tube 71, which can be shown by a pressure measuring element, can indicate that the balloon 55 is expanded and not perforated. It is also possible that the second injecting element 42B will include a pressure measuring element 43 that will indicate when the balloon 55 emerges out of the cannula 33 and that it is not perforated. Afterwards the balloon 55 can be deflated by the second injecting element 42B and the first injecting element 42A activated by inserting and extracting the flowable material 60 from the sinus to validate the integrity of the Schneiderian membrane 25 as described above.

The balloon can be fixated to cannula by various methods like gluing and/or using ligatures and/or using elastic bands and/or welding. The balloon 55 can be also one-piece with the connector 47 if for example the connector and the balloon are made from silicon.

The connector 70 with the balloon 55 can be connected to the cannula 33 before the insertion of the cannula 33 inside the alveolar ridge bone 26. In this case there is no need to connect and disconnect the filling tubes 71, 72 from the cannula 33 during the treatment. The method of using the device can be as follows: The cannula 33 with the filling tubes 71, 72 which are connected to the injecting elements 42A, 42B, can be inserted by the stabilizing tool 45, which can function as a rotating tool or by a ratchet, inside the alveolar ridge bone 26. Then the first injecting element 42A can be activated to increase the pressure. Then the cannula 33 can be advanced to perforate the floor of the maxillary sinus 24 and the pressure drops. Then the first injecting element 42A can be activated again to insert more flowable material 60 inside the sinus to elevate more the Schneiderian membrane 25. Then the first injecting element 42A can be activated to extract the flowable material 60 from the sinus to validate that the Schneiderian membrane 25 is not perforated. Then the first injecting element 42A can be activated again to insert again the flowable material 60 inside the sinus. Then the cannula 33 can be inserted deeper above the floor of the maxillary sinus 24. Then the second injecting element 42B can be activated to inflate the balloon 55 inside the maxillary sinus while being surrounded by the flowable material 60 to further elevate the Schneiderian membrane 25. Then the first injecting element can be activated to validate that the balloon is not perforated by the increasing pressure. Then the second injecting element 42B can be activated to deflate the balloon 55. Then the first injecting element 42A can be activated to validate the integrity of the Schneiderian membrane 25 and to extract the flowable material 60 from the maxillary sinus.

Since the connector 70 can be connected to the cannula 33 during the entire procedure of elevating the Schneiderian membrane 25, there are many optional types of connectors. The cannula can have an internal thread at its proximal part and the connector can have compatible external thread at its distal part to enable screwing the connector inside the cannula. In this configuration the connector can press the base of the balloon inside the cannula. The cannula can have an external thread at its proximal part and the connector can have compatible internal thread at its distal part to enable screwing the connector over the cannula. In this configuration the connector can press the base of the balloon inside the cannula and/or outside the cannula.

The anti-rotational element for inserting the cannula 33 was described to be part of the cannula 33. The anti-rotational element can be also part of the connector 70 if the connector being connected to the cannula in anti-rotational manner or if the connector 70 being screwed with high torque to the cannula 33, before inserting the cannula 33 inside the alveolar ridge bone 26.

Figure 25:
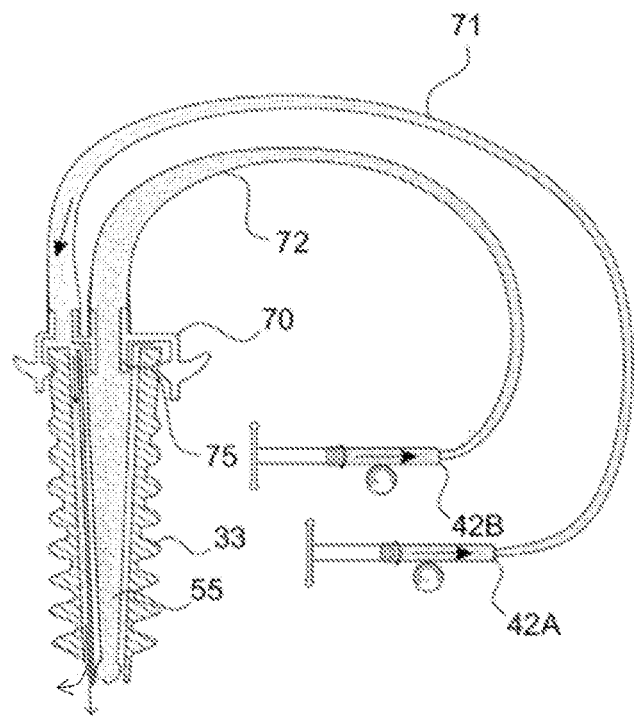
FIG. 25 is a sectional view illustrating an embodiment of assembling an embodiment of a cannula, an embodiment of a balloon, an embodiment of a connector and embodiments of injecting elements.

In another embodiment the cannula 33 has inside two separate channels as illustrated in FIG. 25. A first channel for the insertion of the flowable material and a second channel for the balloon 55. The second channel can be wider than the first channel. The drilling inside the cannula to perforate the floor of the maxillary sinus 24 can be done through the second channel. The connector 70 can have two tubes 71, 72 as described above. A first tube 71 for the insertion of the flowable material through the first channel and the second tube 72 to inflate the balloon 55 in the second channel. The wider base of the balloon can be perforate or part of it missing so the proximal opening of the first channel will be open to allow the entrance of the filling material or the entrance of a needle inside the first channel. The connector 70 can have a distally protruding tube 75 that can be inserted inside the proximal opening of the balloon 55 and seal it. The balloon 55 can be placed over the second distally protruding tube 75 in a water tight manner so the material for expanding the balloon 55 will not leak outside the balloon 55 and/or pass through the first channel.

This distally protruding tube 75 can be continuous with the second tube 72 of the connector. This distally protruding tube 75 can be longer so it will support the balloon 55 during its insertion inside the cannula 33 and prevent folding of the balloon and blocking of the cannula during extraction of the flowable material from the maxillary sinus. The distal end of the distally protruding tube 75 can be adjacent the distal end of the balloon 55. This distally protruding tube 75 can assist also in filling the balloon 55 with a second flowable material before connecting the second tube 72 to reduce the amount of air in the balloon 55. The insertion of the balloon 55 can seal the second channel.

Figure 26:
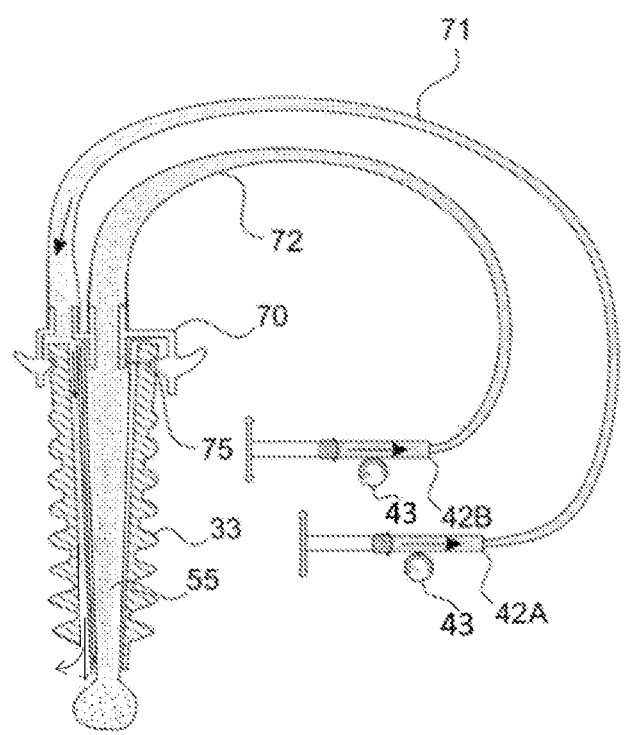
FIG. 26 is a sectional view illustrating an embodiment of assembling an embodiment of a cannula, an embodiment of a balloon, an embodiment of a connector and embodiments of injecting elements after expanding the balloon.

In this embodiment it is possible to inflate the balloon 55 and insert the first flowable material around the balloon 55 simultaneously and/or separately without the need to connect and disconnect the connector 70 and/or deflate the balloon 55, while changing from insertion and/or extraction of the flowable materials for expansion and/or deflation of the balloon 55 and vice versa. Because the balloon 55 being in a separate channel it doesn't block the passage of the flowable material in the first channel. The cannula 33 can have a side perforation at the first channel adjacent the distal end 36 of the cannula 33. The external side wall of the cannula 33 in the first channel can be shorter than the internal side wall of the first channel (adjacent the second channel) so the flowable material can exit the first channel even if the balloon being expanded as illustrated by the arrows in FIGS. 25, 26. The second injecting element 42B can have a pressure measuring device 43 to indicate when the balloon emerges out from the cannula 33 and that the balloon 55 is not perforated.

The distal end 36 of the cannula 33 can have a non-straight or non-flat shape. The second channel can be for example longer distally than the first channel so when the balloon 55 is inflated it will not occlude the distal opening of the first channel. The first channel can have also an opening on the side wall of the first channel close to the distal end of the first channel so if the distal opening of the first channel is occluded the flowable material can still be inserted without producing high pressure in the first tube 71. The distance between the distal opening and the side opening of the first channel can be 0.2-2 mm or 0.4-1.5 mm or 0.5-1.0 mm. The cannula 33 can be inserted so the distal end of second channel is about 1.0-1.5 mm above the floor of the maxillary sinus 24, the distal end of the first channel is about 0.5-1.0 mm above the floor of the maxillary sinus 24 and the side perforation of the first channel is about 0.1-0.5 mm above the floor of the maxillary sinus 24.

In the embodiments of the cannula 33 having two separate channels the proximal part of the cannula 33 and the distal part of the connector 70 can have a non-circular configuration to allow the connection between the connector 70 and the cannula only in a predetermined relation so the first tube 71 will be above the first channel and the second tube 72 will be above the second channel.

In another embodiment the cannula 33 has one channel and the connector 70 as illustrated in FIG. 27 has an elongated projection 78 along one side of the balloon 55. When connecting this connector 70 to the cannula 33 as illustrated in FIG. 28 the elongated projection 78 of the connector 70 separates the space inside the cannula 33 to two regions—one for the balloon 55 and one for the flowable material outside the balloon 55. This is similar to the two separates channels in the cannula 33 in FIGS. 25-26 although the two regions are not completely separated. The elongated projection 78 can protrude distally to the distal end of cannula in about 0.2-1.0 mm, however this can interfere with the insertion of the cannula. If one side of distal end of the cannula is shorter than the other side of the distal end of the cannula 33, the elongated projection can be longer than the shorter side of the cannula and shorter than longer side of the cannula. In this configuration the elongated projection can be placed adjacent the shorter side of the cannula 33. It is also possible that the distally protruding tube 75 will be longer so its distal end will be adjacent the distal end of the balloon 55 as illustrated in FIG. 28. In this embodiment, as in the embodiment above, the flowable material can be inserted even when the balloon 55 being expanded and/or deflated. The cannula 33 can have several perforations adjacent the distal end 36 of the cannula 33 so the flowable material will exit the cannula in case the distal opening is blocked by the balloon 55. The connector 70 can be connected without taking care to the relations between the cannula 33 and the connector 70. The connector 70 can be also connected in a screwed connection.

In another embodiment illustrated in FIG. 29 the connector 70 has two openings. From the first opening a first proximally protruding tube 73 can protrude proximally and a first filling tube 71 can connect the first proximally protruding tube 73 to a first injecting element 42A (not illustrated). From the second opening can protrude proximally a second proximally protruding tube 74 and a second filling tube 72 can connect the second proximally protruding tube 74 to a second injecting element 42B (not illustrated). At least one of the proximally protruding tubes 73, 74 can be angled to the longitudinal axis of the cannula 33 and/or to be curved. The connection between the second proximally protruding tube 74 and the second filling tube 72 can be by a second connector 100. The distal part 101 of the second connector 100 can have external thread and the second proximally protruding tube 74 can have a compatible internal thread so the second connector 100 can be threaded inside the second proximally protruding tube 74. Before threading the second connector 100 to the second proximally protruding tube 74, the balloon 55 can be inserted through the second proximally protruding tube. The distal region 102 of the second proximally protruding tube 74, which can be located distally to the internal thread of the second proximally protruding tube 74 can be narrower and/or to have an internal projecting ring so the wider base 57 of the balloon 55 will touch the narrower region 102 of the second proximally protruding tube 74 so the base 57 of the balloon 55 will be prevented from entering inside the maxillary sinus. When the second connector 100 being screwed inside the second proximally protruding tube 74, the distal part 101 of the second connector 100 can press the base 57 of the balloon 55 to fixate the balloon 55 and to enable a watertight connection. The proximal part 103 of the second connector 100 can be wider to enable easy screwing of the second connector. The proximal part 103 of the second connector 100 can have an additional proximally protruding tube 104 to enable the connection to the second filling tube 72.

As explained above the filling material can be inserted through the first opening of the connector and through the cannula 33 while the balloon 55 can be inflated through the second opening.

In another embodiment illustrate in FIG. 30 The second proximally protruding tube 74 has an external thread and the distal part 101 of the second connector 100 has internal thread and the base 57 of the balloon 55 being located proximally to the second proximally protruding tube 74 and pressed by a narrower region 102 of the second connector 100 to enable a watertight connection.

Figure 31:
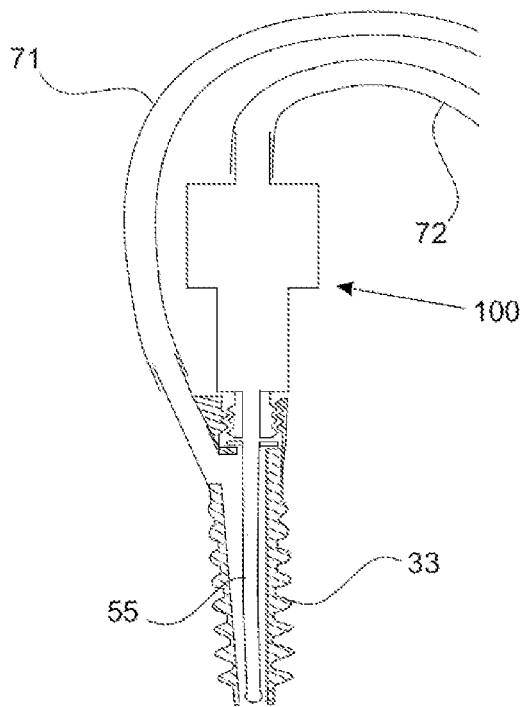
FIG. 31 is a sectional view illustrating an embodiment of assembling an embodiment of a cannula, an embodiment of a balloon, an embodiment of a connector which is part of the cannula and an embodiment of a second connector.

In another embodiment the cannula 33 itself can have two openings so one opening can be connected through a first filling tube 71 to a first injecting element 42A. The balloon 55 can be inserted through the second opening and to be connected to a second injecting element 42B through a second filling tube 72. The connection of the second filling tube 72 can be by a second connector 100 having a screwed connection as illustrated in FIG. 31. In this embodiment the proximal part of the cannula 33 is also the connector so the cannula and the connector are one-piece.

Figure 32:
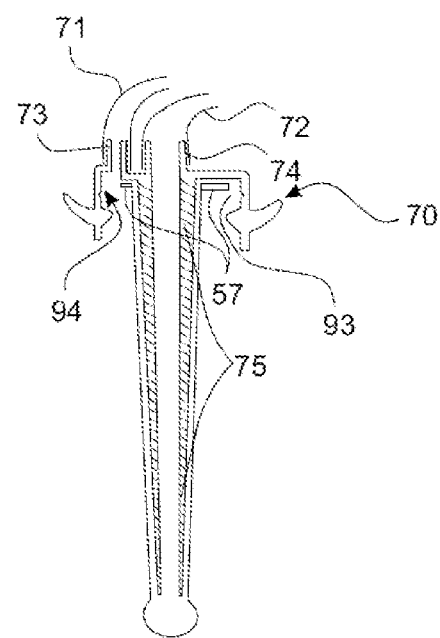
FIG. 32 is a sectional view illustrating an embodiment of a connector having an internal slot and/or intrusions so the balloon can be fixated by a fixating ring.
Figure 33:
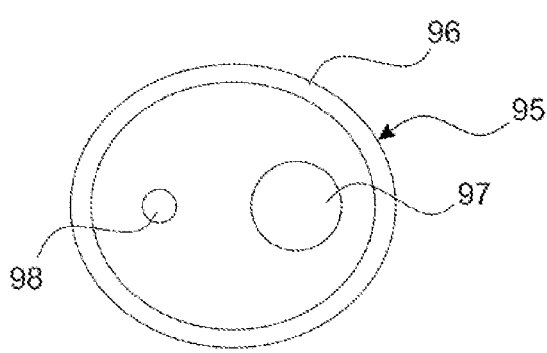
FIG. 33 is a perspective view of a fixating ring that can be used to fixate the balloon in the connector of FIG. 32.
Figure 34:
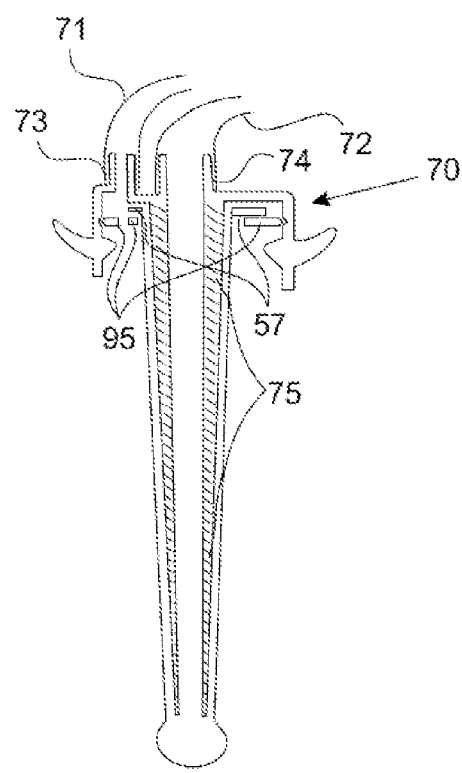
FIG. 34 is a sectional view illustrating the fixating ring of FIG. 33 fixating the balloon to the connector of FIG. 32.

FIGS. 32, 34 and 35 illustrate another option to fixate the balloon 55 to the connector 70. The connector 70 can have a socket 93 that can occupy the entire internal diameter of the connector 70 as illustrated in FIG. 32 or only part of the internal diameter of the connector 70. The balloon 55 can have a base 57 that can occupy the entire socket 93 or only part of the socket 93. The socket 93 can have a slot 94 located distally to the base 57 of the balloon 55. The device can include a fixating ring 95 as illustrated in FIG. 33 that can includes a flexible periphery 96 having a diameter that fits the diameter of the slot 94 inside the connector 70 and being larger than the diameter of the socket 93 so when the fixating ring 95 is pushed inside the socket 93 the body of the balloon 55 pass through the main hole 97 of the fixating ring 95 and the flexible periphery 96 is bended and expanded again to enter the slot 94 so as to fixate the base 57 of the balloon 55 as illustrated in FIG. 34. The flexible periphery 36 of the fixating ring 95 can be along all the periphery of the fixating ring 95 or only along part of the periphery of the fixating ring 95. Similarly, the socket 93 of the connector 70 can have several intrusions located distally to the base 57 of the balloon 55 and the fixating ring 95 can include several flexible protrusions extending laterally more than the diameter of the socket 93 so when the fixating ring 95 is pushed inside the socket 93, the flexible protrusions are bended and expanded again to enter the intrusions so as to fixate the base 57 of the balloon 55.

The fixating ring 95 can include additional hole 98 or several holes to allow the liquid filling material to pass through the fixating ring 95 towards the sinus.

The fixating ring 95 can have a resilient material, for example silicon, nylon and rubber, on its distal side so this material will touch the proximal end of the cannula 33 to improve the sealing between the connector 70 and the cannula 33. This sealing material can be part of the fixating ring 95 or an additional component located distally to the fixating ring 95. The sealing between the connector 70 and the cannula 33 in all the embodiments can be also along the contact between the connector 70 and the external surface of the cannula 33.

In another embodiment the slot 94 and/or the intrusions and the flexible periphery 96 and/or the protrusions of the fixating ring 95 can be located proximally to the base 57 of the balloon 55.

FIG. 35 illustrates another embodiment of a connector 70 in which the first opening 82 for the first liquid filling material being distally to the base 57 of the balloon 55 and the fixating ring 95. In this embodiment the first opening 82 for the first liquid filling material can be at the side wall of the connector 70. The fixating ring 95 can have only one hole 97 as illustrated in FIG. 36.

In all the embodiments it is possible that at least one of the openings in the connector 70 or both openings will be at the side wall of the connector 70. FIG. 37 illustrates an embodiment of a connector 70 having two openings at the side wall of the connector 70. A first opening being connected to the first filling tube 71, a second opening being connected to the second filling tube 72. The proximal part 116 of the connector 70 can have an internal and/or external anti-rotational element so the connector 70 and the cannula can be rotated by a ratchet or any other tool.

In all the embodiments it is possible that the connector 70 will include a distal projection that will touch the inner wall of the cannula 33 so as to seal between the connector 70 and the cannula 33 to prevent the first liquid filling material from leaking proximally outside the cannula 33.

The cannula 33 and the connector 70 can be one piece made for example from titanium or stainless still. It is also possible that one opening leading to one filling tube of the device will be part of the cannula 33 and the second opening leading to the other filling tube twill be part of the connector 70. For example, the opening for the first liquid filling material will be part of the connector 70 and the opening for the second liquid filling material will be part of the cannula 33.

FIGS. 38, 39, 40 and 42 illustrate embodiments in which the cannula 33 has two proximal openings (or more). A first proximal penning 114 for the first liquid filling material and a second proximal opening 115 for the second liquid filling material. The first proximal opening can be connected to the first filling tube 71 by a first connector 120. The second proximal opening 115 can be connected to the second filling tube 72 by a second connector 121.

Figure 39:
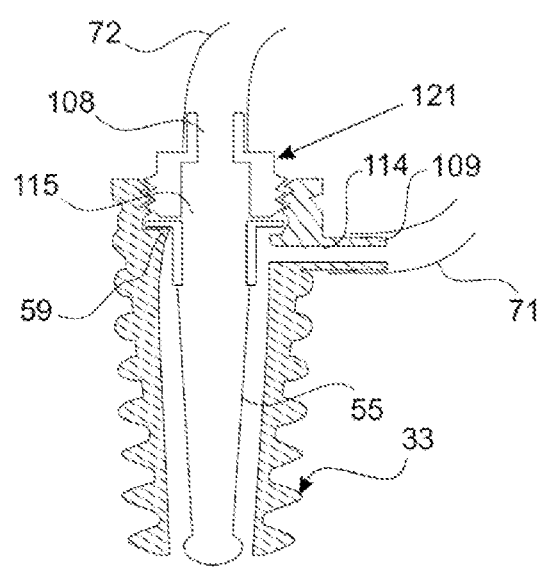
FIG. 39 is a sectional view illustrating an embodiment of cannula that has two proximal openings. The second proximal opening is connected to the second filling tube through a connector which is screwed to the cannula.

The first and or second proximal openings 114, 115 of the cannula 33 can be connected directly to the filling tubes 71, 72. FIG. 38 illustrates an embodiment in which the second connector 121 is connected to the second proximal opening 115 of the cannula 33 in a snap connection and FIG. 39 illustrates an embodiment in which the second connector 121 is connected to the second proximal opening 115 of the cannula 33 in a screwed connection. Other connections can also be used for example connection by friction or by glue. The second proximal opening 115 in FIGS. 38 and 39 is at the proximal end of the cannula 33, but the second proximal opening 115 can be also along the side wall of the cannula 33.

FIG. 38 illustrates a cannula 33 that has a first proximal opening 114 at a side wall of the cannula 33 distally to the second proximal opening 115 at the proximal end of the cannula 33. The first proximal opening 114 being connected through a first filling tube 71 to the first injecting element 42A (not shown) having the first liquid filling material. A tube 122 can protrude from the first proximal opening 114 of the cannula which can be connected to the first filling tube 71. The second connector 121 has a balloon 55 which is fixated to the connector 121 by a fixating ring 95 like the ring which is illustrated in FIG. 36. The fixating ring 95 is compressing the base 57 of the balloon 55 to the connector 121. The proximal part of the cannula 33 can have an internal slot 106 and the connector 121 can have a distal flexible extension 107 that enter the slot 106 of the cannula 33 to fixate the connector 121 to the cannula 33. The connector 121 can be designed to seal the connection between the connector 121 and the cannula 33. The connector 121 can include a resilient material like silicon to touch the connector 121 and the cannula 33 and seal the connection. The connector 121 has a proximal opening 108 proximally to the cannula 33 being connected through a second filling tube 72 to the second injecting element 42B (not shown) having the second liquid filling material.

The connector 121 and/or the fixating ring 95 and/or the cannula 33 can include a separating extension 110 that will be located between the balloon 55 and the first proximal opening 114 of the cannula 33 to prevent the balloon 55 from closing the first proximal side opening 114 when the first liquid filling material is taken out from the sinus. This separating extension 110 can be like a tube and also to assist in the insertion of the fixating ring 95 inside the connector 121 if it is part of the fixating ring 95 as illustrated in FIG. 38.

FIG. 39 illustrates another embodiment of a device in which the first proximal opening 114 of the cannula 33 is at the side wall of the cannula 33 and the second proximal opening 115 is at the proximal end of the cannula 33. In this embodiment the second connector 121 is connected to the cannula 33 by a screwed connection and the base 57 of the balloon 55 being compressed between the second connector 121 and the cannula 33. The proximal part of the cannula 33 can have an internal thread and the distal part of the second connector 121 can have an external thread as illustrated in FIG. 39 or the proximal part of the cannula 38 can have an external thread and the distal part of the second connector 121 can have an internal thread.

The proximal part of the balloon 55 adjacent the first proximal opening 114 of the cannula 33 in FIGS. 38 and 39 can be stiffer than the distal part of the balloon 55 as illustrated in FIG. 39 so the balloon 55 will not close the first proximal opening 114 of the cannula 33 when the first liquid filling material is taken out from the sinus. It is also possible that the proximal part of the balloon 55 adjacent the first proximal opening 114 of the cannula 33 will be inside a separating tube which can be part of the second connector 121 and\or the cannula 33 or can be a separate element of the device.

The base 57 of the balloon 55 can be made at least partially from a different material than the body of the balloon 55. The base 57 of the balloon 55 can be thicker and/or stiffer than body of the balloon 55. The balloon can be also fixated by inserting the base 57 of the balloon 55 inside the slot 94 in the connector 70, 121 without using a fixating ring 95.

Figure 40:
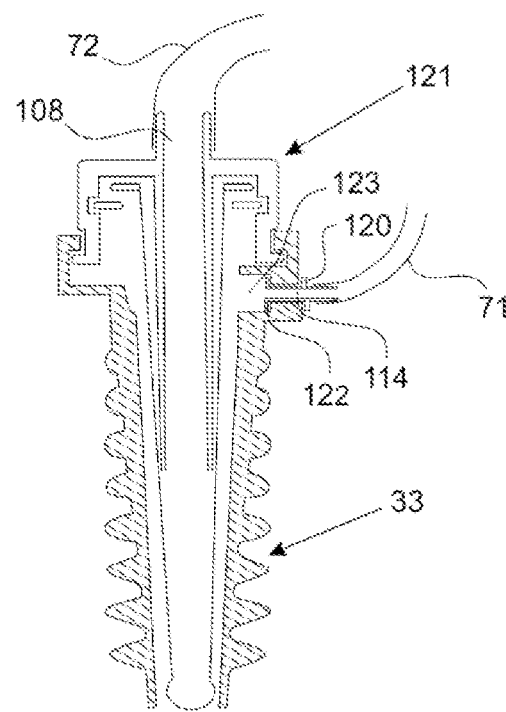
FIG. 40 is a sectional view illustrating an embodiment of cannula that has two proximal openings. The first proximal opening is connected to the first filling tube through a first connector which is connected to the cannula by a snap connection. The second proximal opening is connected to the second filling tube through a second connector which is connected to the cannula by a snap connection.

FIGS. 38 and 39 illustrate embodiments in which the cannula 33 and/or the second connector 121 include protruding tubes 109, 108 which are connected to at least one of the filling tubes 71, 72. It is also possible that at least one of the connectors and/or the cannula 33 include sockets and/or internal tubes and the at least one of the filling tubes 71, 72 is inserted inside the socket and/or the internal tubes. The connection between at least one of the filling tubes 71, 72 and a socket and/or internal tube of the cannula 33 and/or at least one of the connectors can be through an adaptor and/or an additional connector that will be inserted inside the socket and/or the internal tube. FIG. 40 illustrates an embodiment in which the second connector 121 has a protruding tube 108 which is connected to the second filling tube 72 and the cannula 33 has an internal tube at the first proximal opening 114 which is connected to the first filling tube 71 by a first connector 120 which is inserted inside the internal tube at the first proximal opening 114 of the cannula 33. The first connector 120 can include a wider flexible distal part 122 that will be compressed during insertion and expanded again inside a wider space 123 located more inside the cannula 33 so as to fixate the first connector 120. The first connector 120 can also include a sealing element 124 to seal the first proximal opening 114 of the cannula 33. The connection of the first connector 120 can be a detachable connection. It can be also a screwed connection for example a Luer connection and/or any other known connection of tubes.

Figure 41:
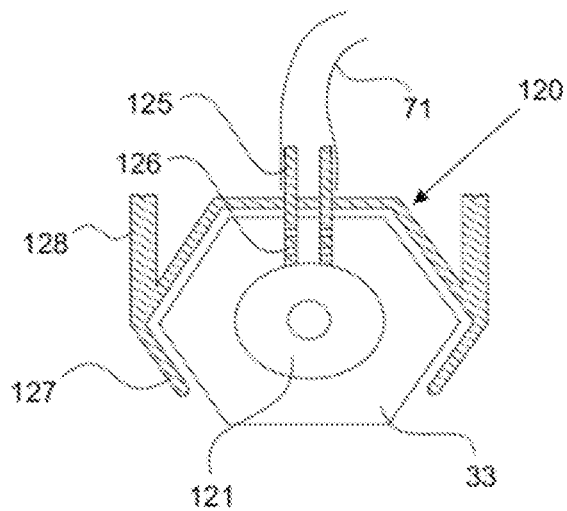
FIG. 41 is a proximal view illustrating an embodiment of a first connector which is connected to the cannula from the side.

The first connector 120 can be also fixated to the external surface of the cannula 33 instead and/or in addition of being fixated inside the cannula 33. FIG. 41 illustrates a proximal view of an embodiment of a first connector 120 being fixated to the proximal part of the cannula 33. The first connector 120 has a protruding tube 125 or a socket to be connected to the first filling tube 71. The proximal part of the cannula 33 has an external anti rotational configuration for example a hexagonal shape as illustrated in FIG. 41. The first connector 120 being connected from the side to the proximal part of the cannula 33. The first connector 121 can have a protruding tube 126 to be inserted through the first proximal opening 114 of the cannula 33. The first connector 120 can have a flexible fixating part 127 that can partially embrace the proximal part of the cannula 33 and to have also a partially hexagonal configuration which is open at one side to allow the proximal part of the cannula 33 to enter inside the fixating part 127 of the first connector 120 from the side. The fixating part 127 of the first connector 120 can include holding projections 128 that enable bending the fixating part 127 of the first connector 120 to allow easy connecting and disconnecting of the first connector 120 to and/or from the cannula 33.

Figure 42:
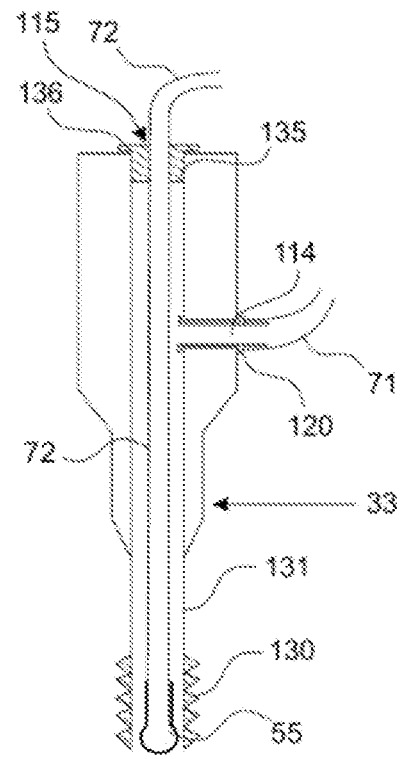
FIG. 42 is a sectional view illustrating an embodiment in which the second filling tube being inside the cannula.

FIG. 42 illustrates an embodiment in which the cannula 33 can be longer having a distal screwed region 130 to be inserted inside the alveolar ridge and middle region 131 to protrude to the oral cavity and a hand holding region 132 that can be rotated directly with the dentist's hand without a ratchet. The cannula 33 can have two proximal openings. A first proximal opening 114 being connected to the first filling tube 71 directly or by a first connector 120. The second filling tube 72 being connected to the balloon 55 and inserted through the second proximal opening 115 of the cannula 33. Each proximal opening 114, 115 can be at the proximal end of the cannula 33 and/or at a side wall of the cannula 33. Both filling tubes 71, 72 can be also connected to the same proximal opening. The balloon 55 can be connected to the second filling tube 72 by glue, heat, mechanical attachment and any other means known in the medical field to connect balloons to tubes. The balloon 55 and the second filling tube 72 can be also made from the same materials to form one continuous component. The second filling tube 72 can include a sealing element 135 that can be inserted inside the cannula 33 and seal it so when the first liquid filling material is inserted it will enter the maxillary sinus and elevate the Schneiderian membrane and will not leak through the second proximal opening 115. The second filling tube 72 can also include a stopper 136 to ensure the balloon 55 is adjacent the distal end of the cannula 33 and to prevent unintentional advancement of the balloon 55 beyond the distal end of the cannula 55 that might tear the Schneiderian membrane. However the balloon 55 can slightly (0.5-5 mm) protrude distally to the distal end of the cannula before being expanded. The stopper 136 can be part of the sealing element 135. The presence of the second filling tube 72 inside the cannula 33 while the balloon 55 being at the distal part of the cannula 33 prevents the balloon 55 from closing the first proximal opening 114 when extracting the liquid filling material from the cannula 33.

In another embodiment the first and second proximal openings 114, 115 are both located at the side walls of the cannula so the cannula has three proximal openings—a first proximal opening for the first liquid filling material to be inserted inside the sinus, a second proximal opening for the second liquid filling material to be inserted inside the balloon and a third opening at the proximal end of the cannula 33. The third opening can be closed during the insertion of the first liquid filling material and later the third opening can be used for filling the sinus with a bone augmenting material.

In all the embodiments it is possible that at least one of the filling tubes being inside the cannula 33.

In all the embodiments it is possible that the connector has a first anti-rotational element that is in contact with the anti-rotational element of the cannula, while the anti-rotational element of the cannula can be inside the cannula and/or outside the cannula. The connector can have a second anti-rotational element so when rotating the second anti-rotational element of the connector the cannula is also rotated. If the connector is used to rotate the cannula it is recommended that the connector will be made from a strong and rigid material foe example metal, titanium, stainless still, plastic, PEEK and any combination of materials.

In all the embodiments it is possible that the largest diameter of the connector is larger than the largest diameter of the cannula. In all the embodiment it is possible that the largest diameter of the connector is equal to the largest diameter of the cannula. In all the embodiment it is possible that the largest diameter of the connector is smaller than the largest diameter of the cannula.

In all the embodiments it is possible to insert the cannula already connected to connector or to insert the cannula first and then to connect the connector. It is also possible to insert the cannula while having an temporary occluding element inside the cannula to prevent bone particles from entering the cannula during insertion of the cannula, since such particles can interfere with the expansion of the balloon. The occluding element can be for example a screw and/or a pin occupying the internal cavity of the cannula. The connector and/or the balloon can also serve this function.

In all the above embodiments the device can be used in several positions along the alveolar ridge. In order for the device to function in a second position after using it in a first position the first opening in the alveolar ridge needs to be closed. Otherwise the flowable material will leak through the first opening while being inserted through the second opening and the Schneiderian membrane won't be elevated. The first opening in the alveolar ridge can be closed for example by inserting a dental implant. The first opening in the alveolar ridge can be closed for example by inserting a replica of a dental implant that will be later removed. The first opening can be closed also by a similar cannula in which the proximal opening is closed. The cannula in the first opening in the alveolar ridge can be for example closed by using a plug or cork. The cannula can be closed by a closing element similar to the connector. This closing element can be connected to the cannula similarly to the optional connections of the connector to the cannula as described above, for example a snap connection while this closing element has no openings. So, several cannulas can be used for several locations of inserting the balloon. Each cannula can be used to elevate the Schneiderian membrane as described above and can be closed to allow the other cannulas to function while the cannulas remain in their place during the procedure.

In all the above embodiments the cannula has an external thread. It is also possible that the periphery of the intra-bony part of the cannula will include a resilient material like silicon or rubber instead or in addition to the external thread to seal between the cannula and the bone and/or the gums. The cannula can also include a stopper to further prevent unintentional advancement of the cannula inside the sinus.

In all the above embodiments the central longitudinal of the connector and/or the second connector can be located along the central longitudinal axis of the cannula to enable rotating the cannula by rotating the connector and/or the second connector.

In all the above embodiments the proximal part of the cannula can be wider than the distal part of the cannula.

In all the above embodiments the proximal part of the cannula can be part of the connector or can be the entire connector so the cannula and at least part of the connector are one-piece.

In all the embodiments of the invention the connection between the various elements (tubes, connectors, cannula, injecting element etc.) can be by several options, for example Luer connection, screwed connection, friction connection and connection through additional connectors or adaptors.

Figure 43:
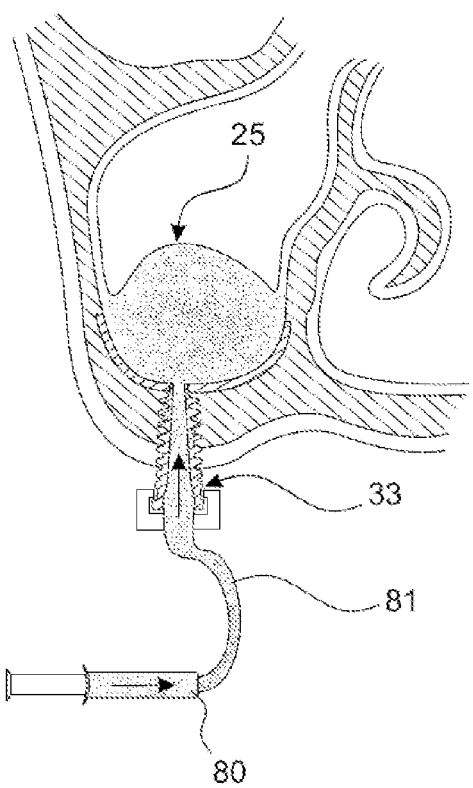
FIG. 43 is a sectional view of the maxillary sinus illustrating the Schneiderian membrane being elevated by the pressurized flowable bone augmenting material.

If the Schneiderian membrane is intact a bone augmentation material can be inserted inside the sinus. The insertion of the bone augmenting material can elevate the Schneiderian membrane 25. The bone augmentation material can be inserted after taking out the cannula 33 and the balloon 55 or can be also injected through the cannula 33 if the bone augmenting material is a flowable as illustrated in FIG. 43. A flowable bone augmenting material can be inside a syringe 80 which is being connected to a shorter filling tube 81. Then the bone augmenting material can be advanced through the short filling tube 81 until filling it completely and there is also almost no air in the short filling tube 81. Then the short filling tube 81 is connected to the cannula 33 and the flowable bone augmenting material can be inserted inside the maxillary sinus. This insertion can elevate the Schneiderian membrane 25.

Figure 44:
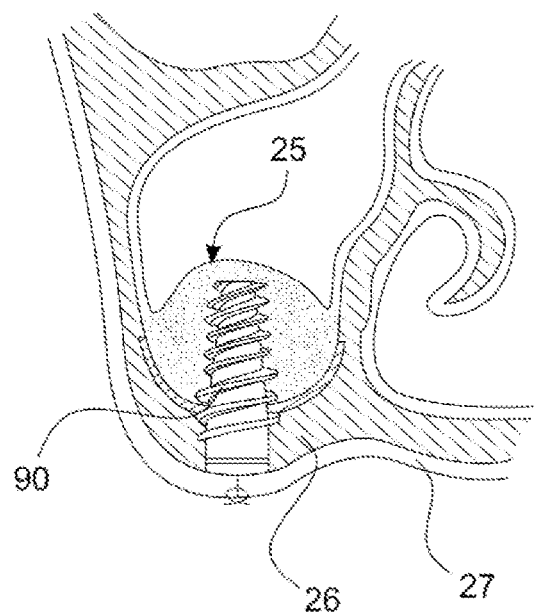
FIG. 44 is a sectional view of the maxillary sinus illustrating a dental implant inserted after elevating the Schneiderian membrane.

After the insertion of the bone augmenting material, the cannula 33 can be taken out and then suturing the gums 27 over the opening in the alveolar ridge bone 26. It is also possible to insert a dental implant 90 after the removal of the cannula 33 as illustrated in FIG. 44. The alveolar ridge bone 26 can stabilize the dental implant 90.

In another embodiment the cannula 33 can be a hollow dental implant which is then inserted deeper inside the sinus and the internal tunnel inside this hollow dental implant can be sealed. It can be sealed for example by a valve, a screw and/or a setting filling material.

The components of the system can be made from a variety of materials used in the medical field and are not limited to special materials or group of materials. The cannula can be made for example from metals and/or plastics, for example stainless steel and/or titanium. The drills can be made for example from metals and/or ceramics. The tubes and their connectors can be made from nylon and/or silicon and/or metal and/or plastic. The balloon can be made for example from rubber and/or silicon. The components of the system can be made also from materials that are for implantation and also from bio-dissipative material. The flowable material to elevate the Schneiderian membrane and the flowable material to expand the balloon and the bone augmentation material can be any material and to include also bioactive materials.

What is claimed is:

1. A device for elevating the Schneiderian membrane of the maxillary sinus to treat the majority of human patients in need for enlargement of the height of a maxillary alveolar ridge bone comprising:
a cannula for insertion through an opening in a human maxillary alveolar ridge bone towards said Schneiderian membrane and a balloon, a distal part of said cannula being sized to be inside the maxillary alveolar ridge of said majority of human patients in need for enlargement of the height of said maxillary alveolar ridge bone, said cannula has an external thread to be engaged with the bony walls of said maxillary alveolar ridge bone below said Schneiderian membrane, at least part of said balloon being inside said cannula, a proximal part of said cannula being connected to a first filling tube so when advancing a first liquid though said first filling tube said first liquid pass through said cannula outside said device inside said maxillary sinus to directly touch and elevate said Schneiderian membrane, said proximal part of said cannula being connected to a second filling tube so when advancing a second liquid though said second filling tube, said second liquid being inserted inside said balloon so as to expand at least part of said balloon distally to a distal end of said cannula inside said maxillary sinus to elevate said Schneiderian membrane while said balloon being in direct contact with said first liquid inside said maxillary sinus, said first filling tube and said second filling tube are both connected to said proximal part of said cannula in a watertight connection so as to prevent leaking out of said first liquid from said maxillary sinus through said cannula while said balloon being expanded inside said maxillary sinus.

2. The device of claim 1, wherein said first liquid is passing between said balloon and the inner wall of said cannula while touching said inner wall.

3. The device of claim 1, wherein the largest external diameter of the most distal 3 mm of said cannula is 2.5-4.7 mm.

4. The device of claim 1 wherein said cannula has an opening at a side wall of said cannula adjacent said distal end of said cannula.

5. The device of claim 1, wherein said distal part of said cannula being tapered to become narrower distally.

6. A device for elevating the Schneiderian membrane of the maxillary sinus to treat normal human patients in need for enlargement of the height of a maxillary alveolar ridge bone comprising:
a cannula sized for insertion inside a normal human maxillary alveolar ridge bone towards said Schneiderian membrane, a connector and a balloon, said cannula has an external thread to be engaged with the bony walls of said alveolar ridge bone below said Schneiderian membrane, at least part of said balloon being inside said cannula, a distal part of said connector being connected to said cannula, a proximal part of said connector has a first opening so when advancing a first liquid though said first opening, said first liquid pass through said cannula inside said maxillary sinus to directly touch and elevate said Schneiderian membrane, said proximal part of said connector has a second opening so when advancing a second liquid though said second opening, said second liquid being inserted inside said balloon so as to expand at least part of said balloon distally to a distal end of said cannula inside said maxillary sinus to elevate said Schneiderian membrane while said balloon being in direct contact with said first liquid inside said maxillary sinus, said distal part of said connector being connected to said cannula in a watertight connection so as to prevent leaking out of said first liquid from said maxillary sinus through said cannula while said balloon being expanded inside said maxillary sinus.

7. The device of claim 6, wherein said first opening of said connector being connected to a first filling tube and said second opening being connected to a second filling tube.

8. The device of claim 7, wherein said at least part of said balloon being expanded and advanced from inside said cannula through said distal end of said cannula along the central longitudinal axis of said cannula.

9. The device of claim 8, wherein said first liquid being laterally to the periphery of said balloon inside said cannula during said advancing of said first liquid.

10. The device of claim 6, wherein said connector being connected to said cannula by a snap connection.

11. The device of claim 6, wherein said connector has a distally protruding tube protruding distally inside said balloon.

12. The device of claim 6, wherein said external thread of said cannula has two external threads each external thread has a thread pitch of 1.5-2.5 mm.

13. A method for displacing the Schneiderian membrane comprising:
   a) performing a path of insertion through the maxillary alveolar ridge bone towards said Schneiderian membrane;
   b) performing through said path of insertion a perforation in the floor of the maxillary sinus while preserving the integrity of said Schneiderian membrane;
   b) inserting through said perforation a liquid to be between said floor of said maxillary sinus and said Schneiderian membrane so as to elevate said Schneiderian membrane;
   d) expanding at least part of a balloon between said floor of said maxillary sinus and said Schneiderian membrane while said balloon is in contact with said liquid and said liquid is prevented from leaking out through said path of insertion so as to further elevate said Schneiderian membrane.

14. The method of claim 13, wherein said liquid being inserted through a cannula which is inserted inside said path of insertion.

15. The method of claim 14, wherein said balloon being inserted through said cannula.

16. The method of claim 15, wherein said cannula being connected to a distal end of a first filling tube in a detachable manner, a proximal end of said filling tube being connected to an injecting element having said liquid, said cannula being connected to a second filling, said balloon being inflated through said second filling tube.

17. The method of claim 16, wherein a distally protruding tube being inside said balloon so the connection between said distally protruding tube and said balloon being watertight.

18. The method of claim 16, wherein said liquid being laterally to the periphery of said balloon inside said cannula during the advancing of said liquid.

19. The method of claim 14, wherein said perforation in the floor of the maxillary sinus is performed by drilling with a drill through said cannula.

20. The method of claim 14, wherein said cannula has an external thread and an anti-rotational element to enable screwing said cannula inside said path of insertion.

* * * * *